United States Patent
Lee et al.

(10) Patent No.: US 12,319,732 B2
(45) Date of Patent: Jun. 3, 2025

(54) ANTI-BETA 1 INTEGRIN HUMANIZED ANTIBODY, AND PHARMACEUTICAL COMPOSITION FOR TREATING CANCER, COMPRISING SAME

(71) Applicant: SG MEDICAL INC., Seoul (KR)

(72) Inventors: Ji Chul Lee, Gyeonggi-do (KR); Jongchan Park, Gyeonggi-do (KR); Sung-Won Min, Seoul (KR); Hyeong Sun Kwon, Seoul (KR)

(73) Assignee: SG MEDICAL INC., Seoul (KR)

( * ) Notice: Subject to any disclaimer, the term of this patent is extended or adjusted under 35 U.S.C. 154(b) by 950 days.

(21) Appl. No.: 17/422,265

(22) PCT Filed: Jan. 8, 2020

(86) PCT No.: PCT/KR2020/000353
§ 371 (c)(1),
(2) Date: Jul. 12, 2021

(87) PCT Pub. No.: WO2020/145669
PCT Pub. Date: Jul. 16, 2020

(65) Prior Publication Data
US 2022/0372132 A1    Nov. 24, 2022

(30) Foreign Application Priority Data

Jan. 10, 2019   (KR) .................. 10-2019-0003213
Jan. 7, 2020    (KR) .................. 10-2020-0002048

(51) Int. Cl.
| | | |
|---|---|---|
| *C07K 16/28* | (2006.01) |
| *A61K 39/00* | (2006.01) |
| *A61P 35/00* | (2006.01) |
| *G01N 33/574* | (2006.01) |

(52) U.S. Cl.
CPC ............ *C07K 16/28* (2013.01); *A61K 39/00* (2013.01); *A61P 35/00* (2018.01); *C07K 2317/24* (2013.01); *C07K 2317/31* (2013.01); *C07K 2317/622* (2013.01); *G01N 33/574* (2013.01)

(58) Field of Classification Search
None
See application file for complete search history.

(56) References Cited

U.S. PATENT DOCUMENTS

| | | |
|---|---|---|
| 8,124,082 B2 | 2/2012 | Fong |
| 10,023,638 B2 * | 7/2018 | Carbonell ............... A61P 29/00 |
| 2019/0309073 A1 | 10/2019 | Saed |
| 2023/0140868 A1 | 5/2023 | Cheresh |

FOREIGN PATENT DOCUMENTS

| | | |
|---|---|---|
| JP | 2007185127 | 7/2007 |
| KR | 1020140030153 | 3/2014 |
| KR | 1020150103094 | 9/2015 |
| KR | 101671069 | 10/2016 |

OTHER PUBLICATIONS

Kim, Min-Young, et al., "Novel monoclonal antibody against beta 1 integrin enhances cisplatin efficacy in human lung adenocarcinoma cells," The Journal of Biomedical Research, 2016, 30(3):217-224.
Aoudjit, F., et al., "Integrin signaling inhibits paclitaxel-induced apoptosis in breast cancer cells," Oncogene (2001) 20, 4995-5004.
Hodkinson, P.S., et al., "ECM overrides DNA damage-induced cell cycle arrest and apoptosis in small-cell lung cancer cells through β1 integrin-dependent activation of PI3-kinase," Cell Death and Differentiation (2006) 13, 1776-1788.
Morozevich, G.E., et al., "The Role of β1 Integrin Subfamily in AnchorageDependent Apoptosis of Breast Carcinoma Cells Differing in Multidrug Resistance," Biochemistry (Moscow), 2006, vol. 71, No. 5, pp. 489-495.
Park, C.C., et al., "β1 Integrin Inhibition Dramatically Enhances Radiotherapy Efficacy in Human Breast Cancer Xenografts," Cancer Res. Jun. 1, 2008; 68(11): 4398-4405.
Carbonell, W.S., et al., "β1 Integrin Targeting Potentiates Antiangiogenic Therapy and Inhibits the Growth of Bevacizumab-Resistant Glioblastoma," Cancer Res. May 15, 2013; 73(10): 3145-3154.

* cited by examiner

*Primary Examiner* — Peter J Reddig
*Assistant Examiner* — Sarah A Alsomairy
(74) *Attorney, Agent, or Firm* — DUANE MORRIS, LLP; Gregory M. Lefkowitz; Brandon A. Chan

(57) ABSTRACT

The present invention relates to a monoclonal antibody or fragment thereof that recognizes and binds specifically to beta 1 integrin as an antigen. The present invention also relates to a pharmaceutical composition for preventing or treating cancer including the monoclonal antibody or fragment thereof. The monoclonal antibody of the present invention is useful in preventing or treating cancer due to its ability to inhibit the proliferation and angiogenesis of cancer cells and effectively induce apoptosis.

14 Claims, 16 Drawing Sheets

Specification includes a Sequence Listing.

[Replaced amino acids in heavy chain variable region of P5 and heavy chain variable region of GP5]

| | HFR1 | HFR2 | HFR3 | HFR4 |
|---|---|---|---|---|
| P5 | QVQLQQSGAELMKPGASVKISCKATGYTFS | WIVQRPGHGLEWIG | KATFTADTSSNTASMQLSSLTSEDSAVYYCAL | WGQGTSVTVSS |
| GP5 | QVQLQQSGSELMKPGASVKVSCKASGYTFT | WIVQRPGHGLEWIG | RATFTADTSTDTASMELSSLTSEDSAVYYCAL | WGQGTSVTVSS |

[Replaced amino acids in light chain variable region of P5 and light chain variable region of GP5]

| | LFR1 | LFR2 | LFR3 | LFR4 |
|---|---|---|---|---|
| P5 | DIVMTQAAPSVSVTPGESVSISC | WFLQRPGQSPQLLIY | GVPDRFSGSGSGTAFTLKIRRVEAEDVGVYYC | FGAGTKLELK |
| GP5 | DIVMTQAAPSLSVTPGESVSISC | WYLQKPGQSPQLLIY | GVPDRFSGSGSGTAFTLKIRRVEAEDVGVYYC | FGAGTKLELK |

FIG. 1

FIG. 2B
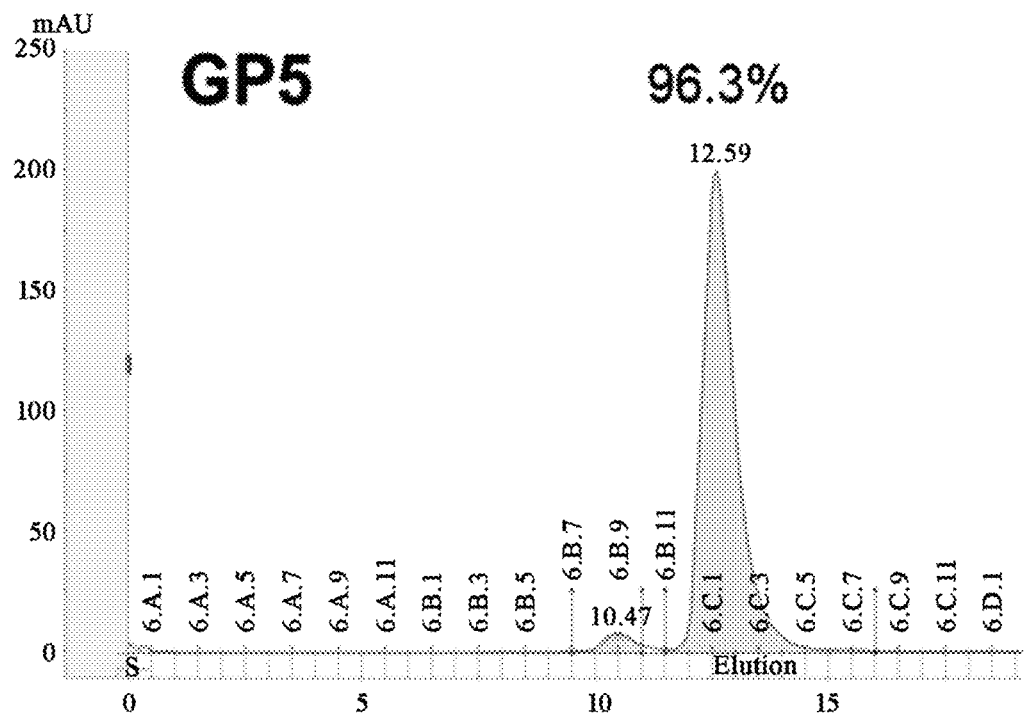
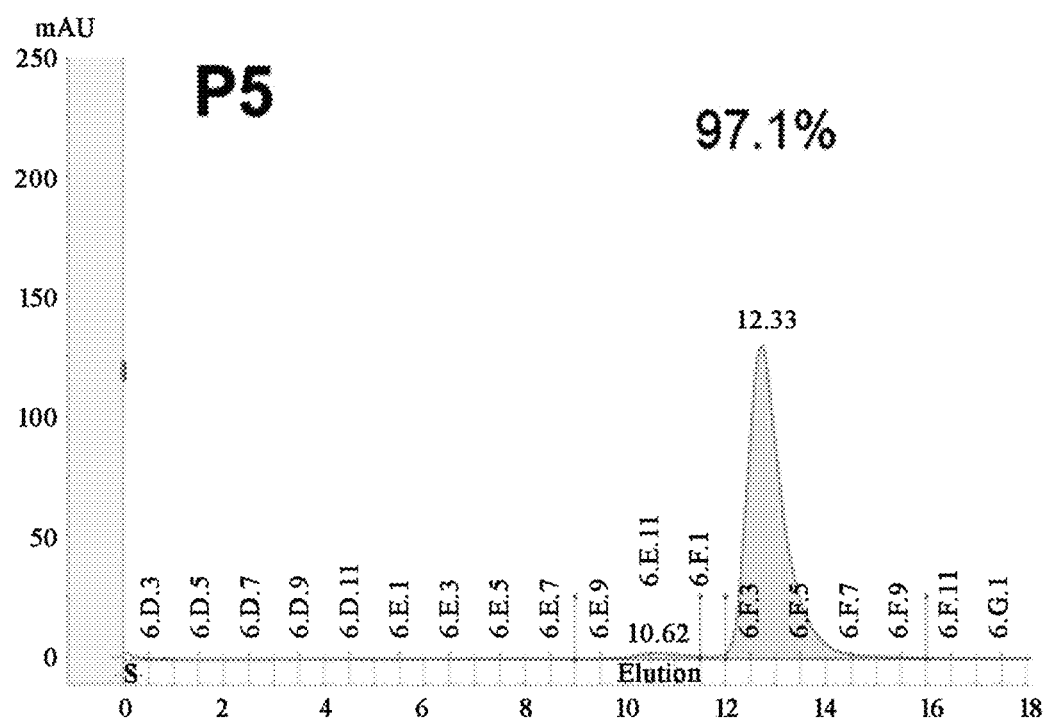

ANTI-BETA 1 INTEGRIN HUMANIZED ANTIBODY, AND PHARMACEUTICAL COMPOSITION FOR TREATING CANCER, COMPRISING SAME

CROSS-REFERENCE TO RELATED APPLICATIONS

This application is a § 371 national stage entry of International Application No. PCT/KR2020/000353, filed on Jan. 8, 2020, which claims priority to Korean Patent Application No. 10-2019-0003213, filed on Jan. 10, 2019, and Korean Patent Application No. 10-2020-0002048, filed on Jan. 7, 2020, the entire contents of which are incorporated herein by reference.

SEQUENCE LISTING

The instant application contains a Sequence Listing, which has been submitted electronically in ASCII format, and is hereby incorporated by reference in its entirety. Said ASCII copy, created on Jan. 16, 2025, is named G1035-20101 ST25 and is 12,242 bytes in size.

TECHNICAL FIELD

The present invention relates to an antibody that specifically binds to beta 1 integrin, which transduces biochemical signals associated with the growth, differentiation, invasion, and metastasis of cancer cells. More specifically, the present invention relates to an antibody that inhibits the signaling function of beta 1 integrin, thus being useful for diagnosis and treatment of various cancers (e.g., non-small cell lung cancer) overexpressing beta 1 integrin.

BACKGROUND ART

The global cancer burden is estimated to have risen to 18 million new cases and 9 million deaths in 2018. One in 5 men and one in 6 women worldwide develop cancer during their lifetime, and one in 8 men and one in 11 women die from the disease. Worldwide, the total number of people who are alive within 5 years of a cancer diagnosis is estimated to be 43.8 million (Press ReleaseNo 263, WHO, Internal Agency for Research on Cancer, 12 Sep. 2018). Lung cancer is one of the three most common cancers with the highest incidence, together with breast cancer and colorectal cancer. According to global cancer statistics in 2018, there were 2.1 million incidence cases of lung cancer and 1.8 million deaths worldwide, accounting for roughly one-fifth (exactly 18.4%) of all cancer deaths (World Health Organization Global Health Observatory Geneva 2018 who.int/gho/database/en/. Accessed Jun. 21, 2018).

Lung cancer is largely divided into small cell lung cancer and non-small cell lung cancer (NSCLC). NSCLC is subdivided into squamous cell lung cancer, adenocarcinoma, and large-cell lung cancer depending on the size and shape of cancer cells. According to the Korean National Cancer Information Center in 2018, carcinoma accounted for 86.6% and sarcoma accounted for 0.2% of all lung cancer cases (24,235) in 2017. The incidence rate of NSCLC is as high as 78% of all carcinoma cases.

Since NSCLC is a very heterogeneous cancer type, its response to anticancer drugs is very low. For this reason, NSCLC is still considered a type of carcinoma with a need for the development of therapeutic agents. Despite genetic and histological studies on lung cancer since the 1950s, platinum-based doublet therapy with cytotoxic drugs was mainly used until the early 2000s. This involves the use of a combination of cisplatin and one of paclitaxel, gemcitabine, and docetaxel or a combination of carboplatin and paclitaxel. However, this therapy is not effective because it is accompanied by systemic side effects and drug resistance.

Since then, several drugs have emerged as targeted therapeutic agents that specifically act on genetic mutations of EGFR, RAS, and ALK. Treatment with EGFR tyrosine kinase inhibitors (TKIs) such as erlotinib, gefitinib, and afatinib is effective for patients with EGFR mutations, but RAS mutations are known to be resistant to these EGFR TKIs. It is also known that Xalkori (crizotinib) is effective for ALK mutations resistant to EGFR TKIs. Therapeutic antibodies such as cetuximab (EGFR target), bevacizumab (VEGF target), and ado-trastuzumab (HER2) have been used for other indications but are not significantly effective for the treatment of lung cancer despite their approval as therapeutic agents for lung cancer. Immuno-oncology drugs targeting PD-1 or PD-L1 have recently emerged but their responsiveness is only about 20-30%. Accordingly, there is a need to develop new therapeutic agents for cancer.

Patients with EGFR mutations show response rates as high as about 70% to EGFR TKIs but most of them acquire drug resistance within 1 year. Potential causes of drug resistance include resistant mutations, alternative splicing, gene amplification, and by-pathway activation. That is, drug resistance is induced in such a way that mutations (for example, EGFR T790M) are newly induced by EGFR TKIs or abnormalities in various signaling systems (for example, HER2 and MET amplifications) occur.

Another important cause of drug resistance is overexpression of beta 1 integrin. Beta 1 integrin is known as a substance that transduces biochemical signals associated with the extracellular environment, particularly growth, differentiation, invasion, and metastatic potential of malignant cells (Juliano R L. The role of beta 1 integrins in tumors [J]. Semin Cancer Biol, 1993; 4(5):277-283.). It is, however, known that aberrant expression of beta 1 integrin affects tumor suppression and progression and increased beta 1 integrin promotes the survival of tumor cells and confers resistance to chemotherapy in several tumor cell types (Hodkinson P S, Elliott T, Wong W S, et al. ECM overrides DNA damage-induced cell cycle arrest and apoptosis in small-cell lung cancer cells through beta1 integrin-dependent activation of PI3-kinase [J]. Cell Death Differ, 2006; 13(10): 1776-1788; Aoudjit F, Vuori K. Integrin signaling inhibits paclitaxel-induced apoptosis in breast cancer cells [J]. Oncogene, 2001; 20(36): 4995-5004; Morozevich G E, Kozlova N I, Preobrazhenskaya M E, et al. The role of beta1 integrin subfamily in anchorage-dependent apoptosis of breast carcinoma cells differing in multidrug resistance[J]. Biochemistry (Mosc), 2006; 71(5): 489-495.). Beta 1 integrin is known as a substance associated with resistance to radiotherapy (Park C C, Zhang H J, Yao E S, Park C J, Bissell M J. Beta1 integrin inhibition dramatically enhances radiotherapy efficacy in human breast cancer xenografts. Cancer Res, 2008; 68(11): 4398-405.). Beta 1 integrin is also known to be associated with resistance to cancer therapy inhibiting angiogenesis using bevacizumab (Carbonell W S, DeLay M, Jahangiri A, Park C C, Aghi M K. β1 integrin targeting potentiates antiangiogenic therapy and inhibits the growth of bevacizumab-resistant glioblastoma. Cancer Res, 2013; 73(10): 3145-54.). High sensitivity of beta 1 integrin silenced cells to cisplatin, a platinum-based drug, and gefitinib, an EGFR TKI drug, was reported (Morello V, Cabodi S, Sigismund S, Camacho-Leal M P, Repetto D, Volante M, Papotti M, Turco E, Defilippi P. β1 integrin controls EGFR signaling and tumorigenic properties of lung cancer cells. Oncogene 2011; 30: 4087-4096.).

Accordingly, resistance to existing therapeutic agents for lung cancer is a problem that needs to be solved. To address this unmet medical need, there arises a need for new drugs that can initially neutralize the causative agents and can be used in combination with existing therapeutic drugs.

The description of the Background Art is merely provided for better understanding the background of the invention and should not be taken as corresponding to the prior art already known to those skilled in the art.

DETAILED DESCRIPTION OF THE INVENTION

Problems to be Solved by the Invention

The present inventors have earnestly and intensively conducted research to develop a novel antibody that specifically binds to beta 1 integrin to maximize its apoptotic activity, and as a result, found that when some amino acids in the sequence of P5 are replaced with other suitable amino acids, maximum anticancer activity can be achieved. The present invention has been accomplished based on this finding.

Therefore, one object of the present invention is to provide a monoclonal antibody or fragment thereof that specifically binds to beta 1 integrin as an antigen.

A further object of the present invention is to provide a multispecific antibody or antibody-drug conjugate (ADC) including the monoclonal antibody or fragment thereof.

Another object of the present invention is to provide a nucleic acid molecule encoding the monoclonal antibody or fragment thereof.

Another object of the present invention is to provide a vector including the nucleic acid molecule.

Another object of the present invention is to provide a host cell including the vector.

Another object of the present invention is to provide a composition including the monoclonal antibody, the nucleic acid molecule or the vector.

Another object of the present invention is to provide a method for quantifying beta 1 integrin in a sample, including treating the sample with the monoclonal antibody or fragment thereof.

Another object of the present invention is to provide a kit for quantifying beta 1 integrin including the monoclonal antibody or fragment thereof.

Still another object of the present invention is to provide a method for providing information for the diagnosis of a disease caused by overexpression of beta 1 integrin.

Other objects and advantages of the invention become more apparent from the following detailed description, claims, and drawings.

Means for Solving the Problems

One aspect of the present invention provides a monoclonal antibody or fragment thereof that recognizes and binds specifically to beta 1 integrin as an antigen.

The present inventors have earnestly and intensively conducted research to develop a novel antibody that specifically binds to beta 1 integrin to inhibit the signaling pathway, and as a result, succeeded in developing a novel antibody with maximum anticancer activity by replacing some amino acids in the sequence of an existing antibody with other suitable amino acids.

Beta 1 integrin is known as a substance that transduces biochemical signals associated with the extracellular environment, particularly growth, differentiation, invasion, and metastatic potential of malignant cells. It is also known that aberrant expression of beta 1 integrin affects tumor suppression and progression and increased beta 1 integrin promotes the survival of tumor cells and confers resistance to chemotherapy in several tumor cell types (Hodkinson P S, Elliott T, Wong W S, et al. ECM overrides DNA damage-induced cell cycle arrest and apoptosis in small-cell lung cancer cells through beta1 integrin-dependent activation of PI3-kinase [J]. *Cell Death Differ*, 2006; 13(10): 1776-1788; Aoudjit F, Vuori K. Integrin signaling inhibits paclitaxel-induced apoptosis in breast cancer cells [J]. *Oncogene*, 2001; 20(36): 4995-5004; Morozevich G E, Kozlova N I, Preobrazhenskaya M E, et al. The role of beta1 integrin subfamily in anchorage-dependent apoptosis of breast carcinoma cells differing in multidrug resistance [J]. *Biochemistry (Mosc)*, 2006; 71(5): 489-495).

Antibodies can be of any type (e.g., IgG, IgE, IgM, IgD, IgA, or IgY) or any subclass (e.g., IgG1, IgG2, IgG3, and IgG4 in humans; and IgG1, IgG2a, IgG2b, and IgG3 in mice) of immunoglobulin molecule. Immunoglobulins, e.g., IgG1, exist in several allotypes. The term "antibody" as used herein is intended to include commonly known isotypes and allotypes. The antibodies described herein are of the IgG1, IgG2, IgG3, or IgG4 subclass or any hybrid thereof (e.g., a hybrid of IgG2 and IgG4).

The term "monoclonal antibody," as used herein, refers to an antibody that displays a single binding specificity and affinity for a particular epitope.

The monoclonal antibody is herein meant to include its fragments. Preferably, the fragments mean antigen binding fragments. The fragment can be prepared by various methods known in the art. For example, Fab and F(ab')2 fragments can be produced by proteolytic cleavage of immunoglobulin molecules, using enzymes such as papain (to produce Fab fragments) or pepsin (to produce F(ab')2 fragments).

The term "fragment" may be a Fab, a Fab', a F(ab')2, a Fv, a single chain Fv (scFv), or a sdAb consisting of a monomeric VH or VL domain. Such fragments are well known in the art.

According to one embodiment of the present invention, the monoclonal antibody or fragment thereof is a single-chain variable fragment (scFv).

Preferably, the monoclonal antibody or fragment thereof of the present invention includes a heavy chain variable region (VH) having the sequence set forth in SEQ ID NO: 3 and/or a light chain variable region (VL) having the sequence set forth in SEQ ID NO: 4.

A VH domain, or one or more CDRs thereof, described herein can be linked to a constant domain for forming a heavy chain. Similarly, a VL domain, or one or more CDRs thereof, described herein can be linked to a constant domain for forming a light chain. A full length heavy chain and full length light chain combine to form a full length antibody.

A further aspect of the present invention provides a multispecific antibody or antibody-drug conjugate (ADC) including the monoclonal antibody or fragment thereof.

The multispecific antibody refers to an antibody or fragment thereof that targets two or more antigens. The multispecific antibody is intended to include bispecific antibodies and trispecific antibodies. For example, the multispecific antibody may be a bispecific antibody having two arms of which one includes the antibody or antigen-binding fragment thereof to beta 1 integrin and the other includes an antigen other than beta 1 integrin.

The antibody-drug conjugate (ADC) refers to a conjugate of the antibody or fragment thereof and a drug. The drug should be stably bound to the antibody until delivery to a target cell and be liberated from the antibody after delivery to the target. In the antibody-drug conjugate of the present invention, the antibody or fragment thereof is conjugated to a drug (e.g., an anticancer agent), for example, by covalent bonding or peptide bonding. Alternatively, the antibody-drug conjugate of the present invention may be in the form of a fusion protein when the drug is a protein.

Another aspect of the present invention provides a nucleic acid molecule encoding the monoclonal antibody or fragment thereof, a vector including the nucleic acid molecule, and a host cell including the vector.

The nucleic acid molecule of the present invention may be an isolated or recombinant nucleic acid molecule. Examples of such nucleic acid molecules include single- and double-stranded DNA and RNA and their corresponding complementary sequences. The isolated nucleic acid may be isolated from a naturally occurring source. In this case, the isolated nucleic acid is separated from the peripheral gene sequence present in the genome of a subject from which the nucleic acid is to be isolated. The isolated nucleic acid may be a nucleic acid, for example, a PCR product, a cDNA molecule or an oligonucleotide, that is enzymatically or chemically synthesized from a template. In this case, the nucleic acid produced from this procedure can be understood as the isolated nucleic acid molecule. The isolated nucleic acid molecule represents a nucleic acid molecule in the form of a separate fragment or as a component of a larger nucleic acid construct. A nucleic acid is "operably linked" when arranged in a functional relationship with another nucleic acid sequence. For example, the DNA of a presequence or secretory leader is operably linked to the DNA of the polypeptide when expressed as a preprotein, which is a presecretory polypeptide. A promoter or an enhancer affecting the transcription of the polypeptide sequence is operably linked to a coding sequence or a ribosome-binding site is operably linked to a coding sequence when it is arranged such that translation is promoted. Generally, the term "operably linked" means that DNA sequences to be linked are located adjacent to each other. In the case of secretory leaders, the term "operably linked" means that the secretory leaders are present adjacent to each other in the same leading frame. However, an enhancer needs not be contiguous. The linkage is performed by ligation at a convenient restriction enzyme site. In the case where this site does not exist, a synthetic oligonucleotide adaptor or a linker is used according to a suitable method known in the art.

As used herein, the term "vector" refers to a carrier into which a nucleic acid sequence can be inserted for introduction into a cell where it can be replicated. A nucleic acid sequence may be exogenous or heterologous. Examples of such vectors include, but are not limited to, plasmids, cosmids, and viruses (e.g., bacteriophage). One of skill in the art may construct a vector through standard recombinant techniques (Maniatis et al., *Molecular Cloning*, A Laboratory Manual, Cold Spring Harbor Press, Cold Spring Harbor, N.Y., 1988; and Ausubel et al., In: *Current Protocols in Molecular Biology*, John, Wiley & Sons, Inc, N Y, 1994, etc.).

As used herein, the term "expression vector" refers to a vector containing a nucleic acid sequence coding for at least part of a gene product capable of being transcribed. In some cases, RNA molecules are then translated into a protein, polypeptide, or peptide. Expression vectors can contain a variety of regulatory sequences. In addition to regulatory sequences that govern transcription and translation, vectors and expression vectors may contain nucleic acid sequences that serve other functions as well.

As used herein, the term "host cell" refers to any transgenic organism that is capable of replicating the vector or expressing the gene encoded by the vector. Suitable organisms include eukaryotes and prokaryotes. The host cell may be transfected or transformed by the vector. The transfection or transformation refers to a process for transferring or introducing the exogenous nucleic acid molecule into the host cell.

The host cell of the present invention is preferably a bacterial cell, yeast cell or animal or human cell (for example, CHO, HeLa, HEK293, BHK-21, COS7, COPS, A549 or NIH3T3 cell), but is not limited thereto.

Another aspect of the present invention provides a composition including the monoclonal antibody or fragment thereof, the nucleic acid molecule or the vector.

According to a preferred embodiment of the present invention, the composition is a pharmaceutical composition for preventing or treating cancer.

The pharmaceutical composition of the present invention may include (a) the antibody or fragment thereof, the nucleic acid molecule or the vector including the nucleic acid molecule and (b) one or more pharmaceutically acceptable carriers.

Another aspect of the present invention provides a method for preventing or treating cancer including administering the pharmaceutical composition.

The type of the cancer to be prevented or treated by the pharmaceutical composition of the present invention is not limited. The pharmaceutical composition of the present invention can be administered to treat a variety of cancers, including: leukemias; lymphomas such as acute lymphocytic leukemia, acute nonlymphocytic leukemias, chronic lymphocytic leukemia, chronic myelogenous leukemia, Hodgkin's disease, non-Hodgkin's lymphomas, and multiple myeloma; childhood solid tumors such as brain tumors, glioblastoma, neuroblastoma, rhabdomyosarcoma, retinoblastoma, Wilms tumor, bone tumors, and soft-tissue sarcomas; and common solid tumors of adults such as lung cancer, breast cancer, prostate cancer, urinary cancers, uterine cancers, oral cancers, pancreatic cancer, melanoma and other skin cancers, stomach cancer, colon cancer, ovarian cancer, brain tumors, liver cancer, laryngeal cancer, thyroid cancer, esophageal cancer, and testicular cancer. More preferably, the pharmaceutical composition of the present invention is administered for treating cancer caused by cancer cells overexpressing beta 1 integrin.

The pharmaceutically acceptable carriers are those that are commonly used for formulation. Examples of the pharmaceutically acceptable carriers include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further include one or more additives selected from the group consisting of lubricating agents, wetting agents, sweetening agents, flavoring agents, emulsifying agents, suspending agents, and preservatives. Details of suitable pharmaceutically acceptable carriers and formulations can be found in *Remington's Pharmaceutical Sciences* (19th ed., 1995).

The pharmaceutical composition of the present invention can be administered orally or parenterally, preferably parenterally. For example, the pharmaceutical composition of the present invention may be administered by intravenous, local or intraperitoneal injection.

A suitable dose of the pharmaceutical composition according to the present invention depends on a variety of factors such as formulation, mode of administration, age, body weight, sex, and pathological condition of the patient, diet, time and route of administration, rate of excretion, and responsiveness. A physician having ordinary skill in the art can readily determine and prescribe an effective dose of the pharmaceutical composition according to the present invention for the desired treatment or prevention. According to a preferred embodiment of the present invention, the daily dose of the pharmaceutical composition according to the present invention is from 0.0001 to 100 mg/kg.

The pharmaceutical composition of the present invention can be prepared in unit dosage forms or dispensed in multi-dose containers with a pharmaceutically acceptable carrier and/or excipient by a suitable method which can be easily carried out by one having ordinary skill in the art. The pharmaceutical composition of the present invention may be in the form of a solution, suspension or emulsion in an oil or aqueous medium. The pharmaceutical composition of the present invention may be in the form of an extract, powder, granule, tablet or capsule. The pharmaceutical composition of the present invention may further include a dispersant or a stabilizer.

The pharmaceutical composition of the present invention can be used for a single therapy. Alternatively, the pharmaceutical composition of the present invention may be used in combination with general cytotoxic chemotherapy or radiotherapy. This combined therapy is more effective for cancer treatment. Particularly, since beta 1 integrin is known to cause resistance to cytotoxic chemotherapy in a variety of cancers (Park C C et al. Cancer Res, 2006, 66(3): 1526-35), the administration of the pharmaceutical composition according to the present invention can provide more significant results in the treatment of cancers resistant to cytotoxic chemotherapy.

Cytotoxic chemotherapeutic agents that can be used with the composition of the present invention include gefitinib, erlotinib, afatinib, lapatinib, dacomintinib, canertinib, neratinib, icotinib, pelitinib, cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastine, and methotrexate.

Radiation therapies that can be used with the composition of the present invention include X-ray irradiation and γ-ray irradiation.

Another aspect of the present invention provides a method for quantifying beta 1 integrin in a sample, including treating the sample with the monoclonal antibody or fragment thereof.

Another aspect of the present invention provides a kit for quantifying beta 1 integrin including the monoclonal antibody or fragment thereof.

The monoclonal antibody or fragment thereof of the present invention can be used to accurately measure the amount of beta 1 integrin in a sample due to its ability to specifically bind to beta 1 integrin.

The use of the quantification method and/or kit according to the present invention enables the quantification of beta 1 integrin by analyzing the antigen to the antibody through an antigen-antibody binding reaction. The antigen-antibody binding reaction is preferably selected from the group consisting of, but not limited to, enzyme-linked immunosorbent assay (ELISA), radioimmunoassay (RIA), sandwich assay, Western blotting on polyacrylamide gel, immunoblotting assay, and immunohistochemical staining.

A support for the antigen-antibody binding reaction is selected from the group consisting of, but not limited to, nitrocellulose membranes, PVDF membranes, well plates made of polyvinyl or polystyrene resin, and slide glasses.

The secondary antibody is preferably labeled with a reagent that develops a color. The color-developing reagent can be selected from the group consisting of fluoresceins and dyes. The fluoresceins may be, for example, horseradish peroxidase (HRP), alkaline phosphatase, colloid gold, poly-L-lysine-fluorescein isothiocyanate (FITC), and rhodamine-B-isothiocyanate (RITC). A substrate for inducing color development is preferably used depending on the color-developing reagent. The substrate is preferably selected from the group consisting of, but not limited to, 3,3',5,5'-tetramethylbenzidine (TMB), 2,2'-azino-bis(3-ethylbenzothiazoline)-6-sulfonic acid (ABTS), and ophenylenediamine (OPD).

Yet another aspect of the present invention provides a method for providing information for the diagnosis of a disease caused by overexpression of beta 1 integrin, including (a) separating a sample from a subject, (b) treating the sample with the monoclonal antibody or fragment thereof, and (c) determining whether the expression level of beta 1 integrin in the sample from the subject is higher than that of beta 1 integrin in a normal sample.

The same explanation of the quantification method and/or kit according to the present invention applies to the method for providing information for the diagnosis of a disease caused by overexpression of beta 1 integrin.

Altered expression of beta 1 integrin affects tumor suppression and progression and increased beta 1 integrin promotes the survival of tumor cells and confers resistance to chemotherapy in several tumor cell types (Hodkinson P S, Elliott T, Wong W S, et al. ECM overrides DNA damage-induced cell cycle arrest and apoptosis in small-cell lung cancer cells through beta1 integrin-dependent activation of PI3-kinase[J]. *Cell Death Differ*, 2006; 13(10): 1776-1788; Aoudjit F, Vuori K. Integrin signaling inhibits paclitaxel-induced apoptosis in breast cancer cells[J]. *Oncogene*, 2001; 20(36): 4995-5004; Morozevich G E, Kozlova N I, Preobrazhenskaya M E, et al. The role of beta1 integrin subfamily in anchorage-dependent apoptosis of breast carcinoma cells differing in multidrug resistance[J]. *Biochemistry (Mosc)*, 2006; 71(5): 489-495.), a comparison of the expression level of beta 1 integrin with that in a healthy subject can provide information for the diagnosis of a disease caused by overexpression of beta 1 integrin.

According to a preferred embodiment of the present invention, the disease caused by overexpression of beta 1 integrin is a cancer.

Effects of the Invention

The features and advantages of the present invention are summarized as follows:

(i) The monoclonal antibody or fragment thereof of the present invention recognizes and specifically binds to beta 1 integrin as an antigen.

(ii) The pharmaceutical composition of the present invention, which includes the monoclonal antibody or fragment thereof, is effective in preventing or treating cancer.

(iii) The monoclonal antibody of the present invention is useful in preventing or treating cancer due to its ability to inhibit the proliferation and angiogenesis of cancer cells and effectively induce apoptosis.

BRIEF DESCRIPTION OF THE DRAWINGS

FIG. 1 shows the amino acid sequences of framework regions (FRs) of a heavy chain variable region (HFR1 (SEQ ID NO: 21); HFR2 (SEQ ID NO: 22); HFR3 (SEQ ID NO: 23); and HFR4 (SEQ ID NO: 24)) and FRs of a light chain variable region (LFR1 (SEQ ID NO: 25); LFR2 (SEQ ID NO: 22); LFR3 (SEQ ID NO: 26); and LFR4 (SEQ ID NO: 24)) of a monoclonal antibody P5 and FRs of a heavy chain variable region (HFR1 (SEQ ID NO: 27); HFR2 (SEQ ID NO: 28); HFR3 (SEQ ID NO: 29); and HFR4 (SEQ ID NO: 30)) and FRs of a light chain variable region (LFR1 (SEQ ID NO: 31); LFR2 (SEQ ID NO: 32); LFR3 (SEQ ID NO: 29); and LFR4 (SEQ ID NO: 30)) of a monoclonal antibody (GP5) according to the present invention.

MODE FOR CARRYING OUT THE INVENTION

Figure 2A:
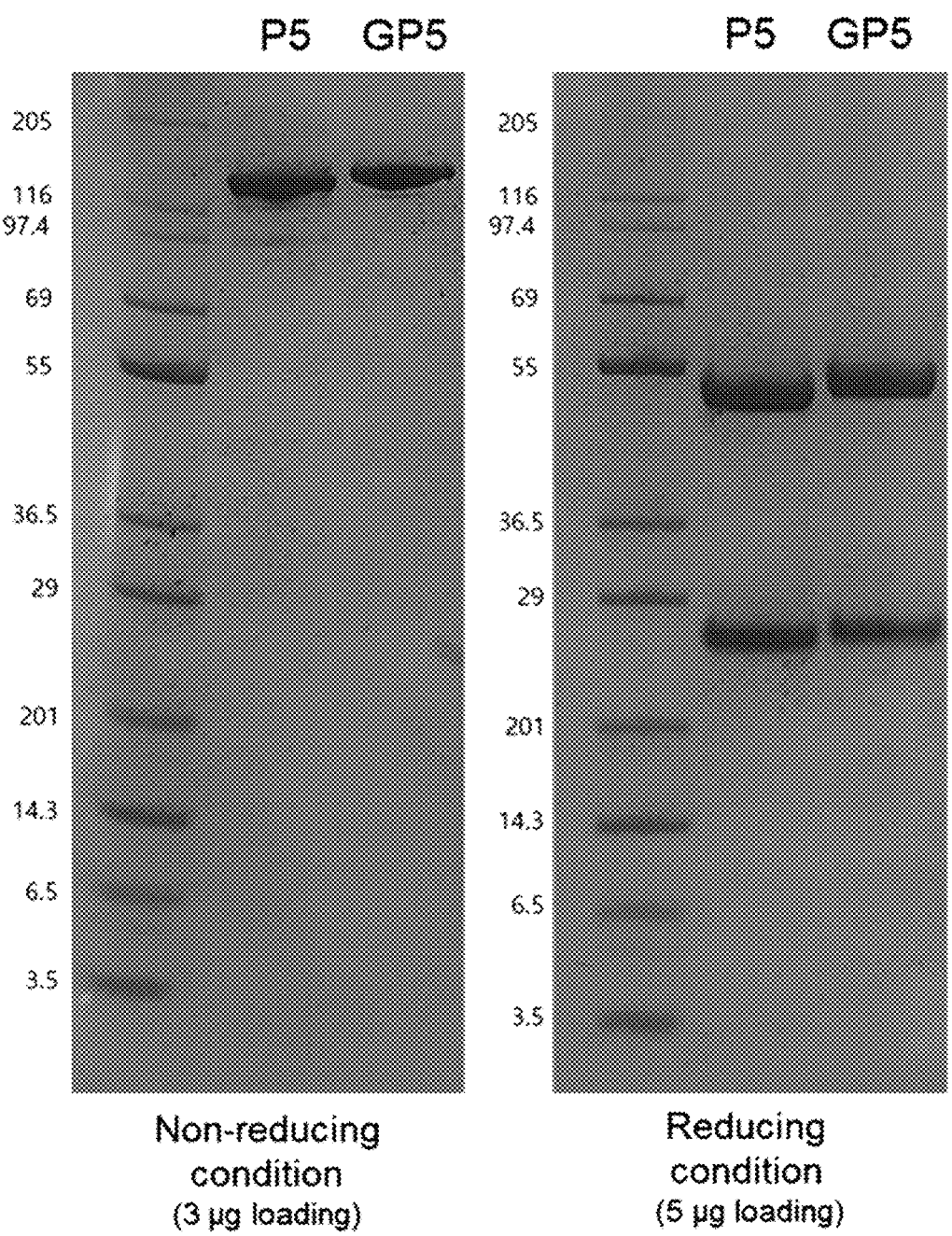
FIG. 2 confirms the purity (FIG. 2A) and homogeneity (FIG. 2B) of a monoclonal antibody (GP5) according to the present invention.

The present invention will be more specifically explained with reference to the following examples. It will be evident to those skilled in the art that the scope of the present invention is not limited by these examples according to the gist of the present invention.

EXAMPLES

<Example 1> Development of Humanized Antibody with Higher Activity for Cancer Apoptosis than P5

The present inventors performed the following experiment to develop a humanized antibody with higher activity for cancer apoptosis than P5 (Kim M Y et al. *J Biomed Res*, 2016, 30(3): 217-24).

For the modification of P5, mutations were introduced into 4 FRs (HFR1, HFR2, HFR3, and HFR4) of the heavy chain variable region and 4 FRs (LFR1, LFR2, LFR3, and LFR4) of the light chain variable region by the following procedure:

1) Specifically, amino acids in HFR1, HFR2, HFR3, and HFR4 were replaced with different amino acids from those in the original antibody using the sequences of IGHV7-4-1*03, IGHV4-30-4*06, IGHV1-69-2*01, and IGHJ6*01, respectively, taking into consideration the similarity or dissimilarity in physicochemical properties of amino acids. The replaced amino acids were I20V, T25S, and S30T in IGHV7-4-1*03, R40H and H43K in IGHV4-30-4*06, K66R, A67V, F69I, S75T, N76D, S79Y, Q81E, T83R, and S87T in IGHV1-69-2*01, and S108T in IGHJ6*01. After the modified heavy chain variable region was again aligned with IGHV1-2*02, mutations expected to have the best performances were selected.

2) Amino acids in LFR1, LFR2, LFR3, and LFR4 were replaced using IGKV2-18*01, IGKV2-18*01, IGKV2-28*01, and IGKJ2*01, respectively, as follows. The replaced amino acids were A8P, V11L, T14N, S18P, and V19A in IGKV2-18*01, R39K in IGKV2-18*01, nothing in IGKV2-28*01, and L106I in IGKJ2*01. After the modified light chain variable region was again aligned with IGKV2D-29*02, mutations expected to have the best performances were selected.

3) The positions of the selected mutations were as follows:

① Heavy chain variable region: A9S, I20V, T25S, S30T, K67R, S76T, N77D, Q82E.

② Light chain variable region: V11L, F41Y, R44K.

(The amino acid residues in the antibody domains are numbered according to the Kabat EU numbering system commonly used in the art (Kabat et al., "Sequences of Proteins of Immunological Interest" 5th Ed., U.S. Department of Health and Human Services, NIH Publication No. 91-3242, 1991).

The antibody was constructed by combining the humanized heavy chain variable region with a human IgG1 heavy chain constant region (CH1, CH2, CH3) and combining the humanized light chain variable region with a human light chain constant region (Ckappa).

Finally, the humanized antibody was called "GP5" and its amino acid sequence is shown in Table 1. Information on the replaced amino acids can be found in FIG. 1.

TABLE 1

Amino acid sequences of P5 and GP5 heavy and light chain variable regions

Heavy chain variable region

P5  QVQLQQSGAELMKPGASVKISCKATGYTFSNYWIEWIVQRPGHGLE
    WIGEILPGSVNTNYNAKFKDKATFTADTSSNTASMQLSSLTSEDSA
    VYYCALATPYYALDSWGQGTSVTVSS (SEQ ID NO: 1)

GP5 QVQLQQSGSELMKPGASVKVSCKASGYTFTNYWIEWIVQRPGHGLE
    WIGEILPGSVNTNYNAKFKDRATFTADTSTDTASMELSSLTSEDSA
    VYYCALATPYYALDSWGQGTSVTVSS (SEQ ID NO: 3)

Light chain variable region

P5  DIVMTQAAPSVSVTPGESVSISCRSTESLLHSNGNTYLYWFLQRPG
    QSPQLLIYRMSNRASGVPDRFSGSGSGTAFTLKIRRVEAEDVGVYY
    CMQHLEYPFTFGAGTKLELK (SEQ ID NO: 2)

GP5 DIVMTQAAPSLSVTPGESVSISCRSTESLLHSNGNTYLYWYLQKPG
    QSPQLLIYRMSNRASGVPDRFSGSGSGTAFTLKIRRVEAEDVGVYY
    CMQHLEYPFTFGAGTKLELK (SEQ ID NO: 4)

In the above table, the positions of the replaced amino acids are highlighted in bold (A9S, I20V, T25S, S30T, K67R, S76T, N77D, Q82E V11L, F41Y, and R44K according to the Kabat EU numbering system).

<Example 2> Conversion of GP5 Clone into Full Antibody and Expression/Purification The DNA of the variable region of GP5 developed in Example 1 was synthesized in the form of scFv (Cosmogenetech, Korea) and converted into a full antibody (IgG) by PCR. First, fragments of the heavy and light chain variable and constant regions were obtained from a scFv-containing pUC vector (Cosmogenetech, Korea) by PCR using combinations of the VH, CH, VL, and CK primers shown in Table 2. The heavy and light chains of GP5 with the variable and constant regions of the antibody were obtained by PCR using combinations of the HC and LC primers shown in Table 2. The heavy chain was treated with EcoRl and NotI (New England Biolab, UK) and ligated into a pCMV vector (Thermo Fisher SCIENTIFIC, USA) for animal cell expression treated with the same restriction enzymes. The light chain was treated with XbaI (New England Biolab, UK) and ligated into a pCMV vector with the same restriction enzyme. The ligated plasmids were transformed to DH5α competent *Escherichia coli* cells (New England Biolab, UK) by the application of a thermal shock, and colonies were obtained and mass cultured to obtain plasmids.

TABLE 2

List of primers used for cloning of GP5 full antibody

| Primer | | Sequence | SEQ ID NO: |
|---|---|---|---|
| $V_H$ | Forward1 | CAG AAT TCA CTC TAA CCA TGG AAT GGA GCT GGG TCT TTC TCT TCT TCC TGT CAG TAA CTA CAG | 5 |
| $V_H$ | Forward2 | CTT CCT GTC AGT AAC TAC AGG TGT CCA CTC CCA GGT GCA ACT GCA GCA GTC | 6 |
| $V_H$ | Reverse1 | CCA GCG TGA CCG TAT CCA GCG CCT CCA CCA AGG GCC CCA | 7 |
| $V_H$ | Reverse2 | CCA GCG TGA CCG TAT CCA GCG CCT CCA CCA AGG GCC CCA | 8 |
| $C_H$ | Forward1 | GGG CCC TTG GTG GAG GCG CTG GAT ACG GTC ACG CTG G | 9 |
| $C_H$ | Reverse1 | GCA TTG TCT GAG TAG GTG TC | 10 |
| HC | Forward1 | CAG AAT TCA CTC TAA CCA TGG AAT GGA GCT GGG TCT TTC TCT TCT TCC TGT CAG TAA CTA CAG | 11 |
| HC | Reverse1 | GCA TTG TCT GAG TAG GTG TC | 12 |
| $V_L$ | Forward1 | AAG CTT CGG CAC GAG CAG ACC AGC ATG GGC ATC AAG ATG GAG ACA CAT TCT CAG GTC TTT GTA TAC AT | 13 |
| $V_L$ | Forward2 | TCT CAG GTC TTT GTA TAC ATG TTG CTG TGG TTG TCT GGT GTT GAA GGA GAT ATT GTG ATG ACT CAG GC | 14 |
| $V_L$ | Reverse1 | GGA CCA AGC TGG AGC TGA AAC GTA CGG T | 15 |
| $V_L$ | Reverse2 | GGA CCA AGC TGG AGC TGA AAC GTA CGG T | 16 |
| $c_k$ | Forward1 | TGG GGC CCT TGG TGG AGG CGC TGG ATA CGG TCA CGC TGG | 17 |
| $c_k$ | Reverse1 | CAT TTT GTC TGA CTA GGT GTC C | 18 |

TABLE 2-continued

List of primers used for cloning of GP5 full antibody

| Primer | | Sequence | SEQ ID NO: |
|---|---|---|---|
| LC | Forward1 | AAG CTT CGG CAC GAG CAG ACC AGC ATG GGC ATC AAG ATG GAG ACA CAT TCT CAG GTC TTT GTA TAC AT | 19 |
| LC | Reverse1 | CAT TTT GTC TGA CTA GGT GTC C | 20 |

Each of the plasmids of the heavy and light chains of the full antibody was transfected into HEK293F cells (Invitrogen, USA) using polyethylenimine (PEI) (Polysciences, USA) and 150 mM NaCl, followed by culture in Freestyle 293 expression medium (Invitrogen, USA) at 37° C. temperature, 8% $CO_2$, and 55% humidity for 7 days. The expressed cell culture was centrifuged at 4,000 rpm for 10 min. The supernatant was collected and filtered through a 0.22 µm filter. The filtrate was allowed to bind to 1 ml of Protein A resin (GenScript, China) at 4° C. The bound resin was washed with 10 cv (column volume) of PBS solution, eluted with 100 mM glycine-HCl (pH 2.7), and neutralized with 1 M Tris-HCl (pH 9.0). After buffer change with PBS at pH 7.2-7.4, the sizes and purities of the light and heavy chains of the purified antibody were determined by SDS-PAGE. The results are shown in FIG. 2A. The molecular weights of the light and heavy chains of the purified monoclonal antibody GP5 were found to agree with theoretical calculations. The purity of the monoclonal antibody GP5 was found to be high. In addition, the homogeneity of the purified antibody was found to be 95%, as determined by size exclusion chromatography (SEC) (GE Healthcare, USA). The results are shown in FIG. 2B.

<Example 3> Analysis of Affinity of the Monoclonal Antibody GP5 for Beta 1 Integrin The affinity of the monoclonal antibody GP5 produced in Example 2 for beta 1 integrin was determined by direct ELISA. Since the monoclonal antibody GP5 is a humanized antibody and P5 is a mouse antibody, each antibody was labeled with HRP using a peroxidase labeling kit-$NH_2$ (Dojindo, Japan) for direct affinity comparison. The direct ELISA was performed by the following procedure. First, each of recombinant human beta 1 integrin (Sino biological, China) and recombinant mouse beta 1 integrin (MyBioSource, USA) was diluted to 1 µg/ml in 50 µl of PBS, plated in a 96-well immune plate (Corning, USA), and stored at 4° C. overnight for its adsorption. After incubation with a buffer containing 3% bovine serum albumin (Millipore, USA) at 37° C. for 1 h, the wells were treated with the HRP-labeled antibody sequentially diluted to concentrations of 0.01, 0.03, 0.1, 0.3, 1, 3, 100, 300, and 1000 nM (50 µl/well). The well plate was incubated at 37° C. for 2 h to allow the antibody to bind to the antigen and washed 3 times with a buffer containing 0.5% Tween 20 (Amresco, USA). 50 µl of 3,3',5,5'-tetramethylbenzidine (TMB) (Life technologies, USA) was plated in each well and allowed to develop color for 30 min. Absorbance was measured at 450 nm using a spectrophotometer (Biotek, USA). The results are shown in FIGS. 3a and 3b.

Figure 3A:
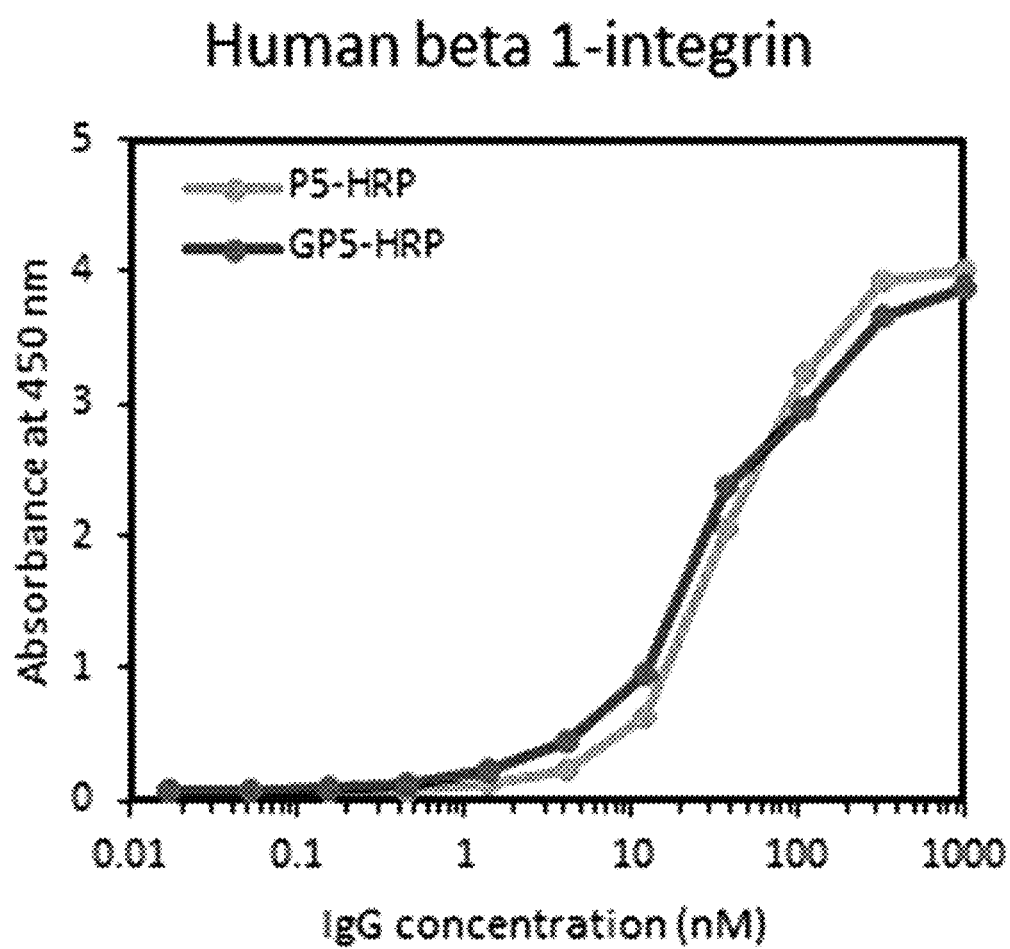
FIG. 3 shows the affinity of a monoclonal antibody (GP5) according to the present invention for recombinant human beta 1 integrin (FIG. 3A), the affinity y of the monoclonal antibody (GP5) for recombinant mouse beta 1 integrin (FIG. 3B), and the specificity of the monoclonal antibody (GP5) for beta 1 integrin (FIG. 3C).
Figure 3B:
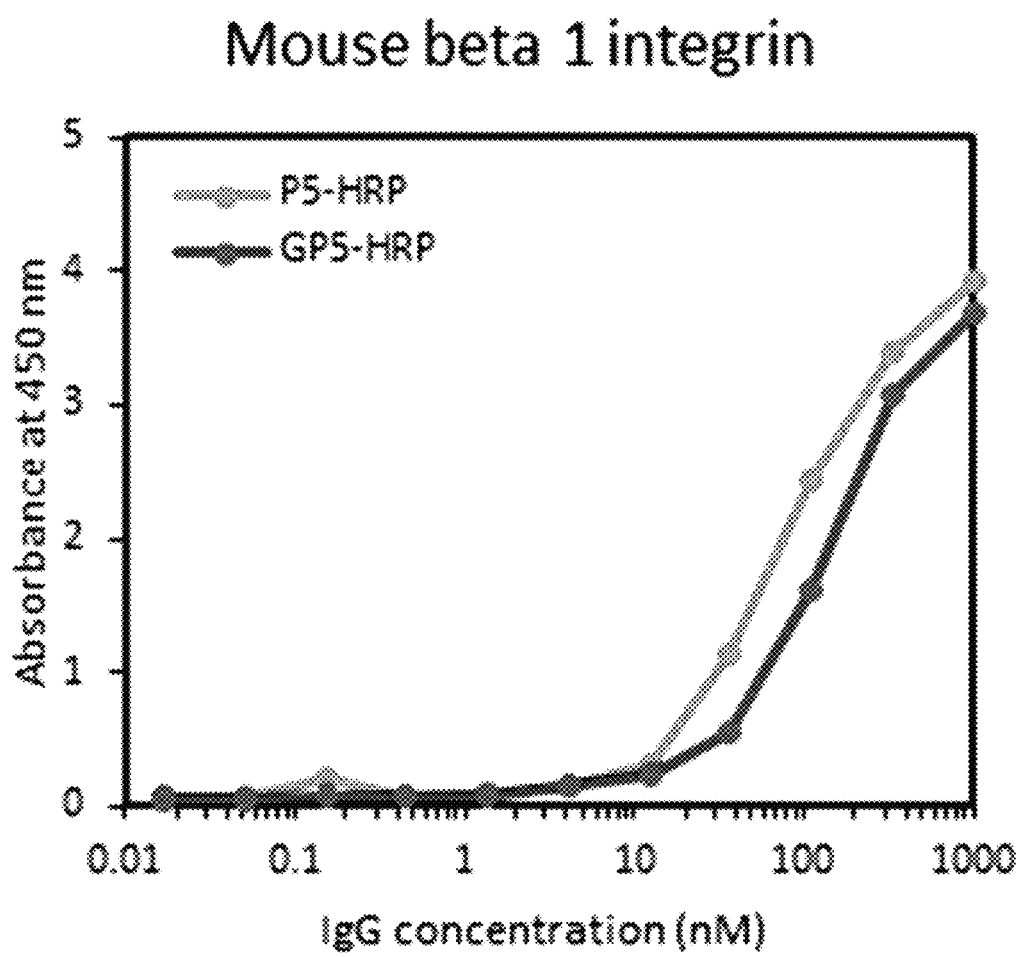

The affinities of the inventive monoclonal antibody GP5 for recombinant human beta 1 integrin and recombinant mouse beta 1 integrin were comparable to those of P5 (FIGS. 3a and 3b).

The affinities of the monoclonal antibody GP5 for various integrins were measured by indirect ELISA to determine the specificity of the monoclonal antibody GP5 for beta 1 integrin. Each of recombinant human αVβ1 integrin (R&D Systems, USA), αVβ3 integrin (R&D Systems, USA), αVβ5 integrin (R&D Systems, USA), αVβ6 integrin (R&D Systems, USA), αVβ8 integrin (R&D Systems, USA), α5β1 integrin (R&D Systems, USA), and α2bβ3 integrin (R&D Systems, USA) was diluted to 1 µg/ml in 50 µl of PBS, plated in a 96-well immune plate (Corning, USA), and stored at 4° C. overnight for its adsorption. After incubation with a buffer containing 3% bovine serum albumin (Millipore, USA) at 37° C. for 1 h, the wells were treated with the monoclonal antibody GP5 sequentially diluted to concentrations of 0.01, 0.03, 0.1, 0.3, 1, 3, 100, 300, and 1000 nM (50 µl/well). The well plate was incubated at 37° C. for 2 h to allow the antibody to bind to the antigen and washed 3 times with a buffer containing 0.5% Tween 20 (Amresco, USA). The wells were treated with HRP-labeled anti-human Fc IgG secondary antibody diluted 1:3000 with PBS (50 µl/well). The well plate was incubated at 37° C. for 1 h and washed 3 times with a buffer containing 0.5% Tween 20 (Amresco, USA). 50 µl of 3,3',5,5'-tetramethylbenzidine (TMB) (Life technologies, USA) was plated in each well and allowed to develop color for 30 min. Absorbance was measured at 450 nm using a spectrophotometer (Biotek, USA). The results are shown in FIG. 3C.

Figure 3C:
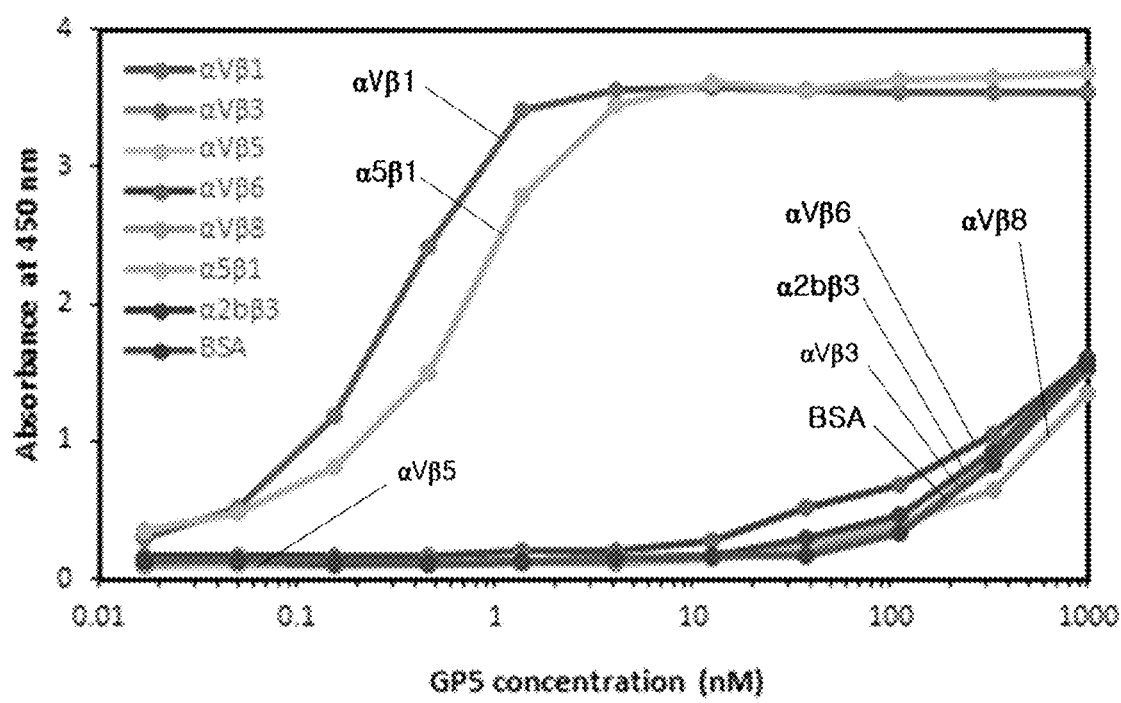

The inventive monoclonal antibody GP5 was found to specifically bind to only integrins whose β chain is beta 1 regardless of their a chain (FIG. 3C).

As demonstrated above, the modified monoclonal antibody (GP5) did not show a decrease in affinity, which is common during antibody humanization, and was specific for beta 1 integrin. Therefore, the modified monoclonal antibody (GP5) is expected to be useful in treating various cancers, including non-small cell lung cancer, like the parent antibody (P5).

<Example 4> Confirmation of Expression of Beta 1 Integrin in Various Cancer Cell Lines, Including Non-Small Cell Lung Cancer Cell Line The present inventors conducted an experiment to confirm the expression of beta 1 integrin in various cancer cell lines, including a non-small cell lung cancer cell line.

Specifically, non-small cell lung cancer cell line A549, breast cancer cell line MDA-MB-231, and colorectal cancer cell line HCT116 were suspended at a density of $5 \times 10^5$ cells/sample in PBS with or without the monoclonal antibody GP5 at a concentration of 10 µg/ml and cultured at 4° C. for 1 h. The culture was centrifuged at 3,500 rpm for 5 min, washed with 200 µl of PBS, and centrifuged again at 3,000 rpm for 5 min. Cells were treated with goat anti-human IgG antibody, Alexa Fluor 488 (ThermoFisher Scientific, USA) diluted 1:200 with PBS, followed by culture at 4° C. in the dark for 30 min. The fluorescently stained cells were washed with PBS, suspended in 500 µl of PBS, and analyzed by flow cytometry using an Attune NxT flow cytometer (ThermoFisher Scientific, USA). The results are shown in FIG. 4.

Figure 4:
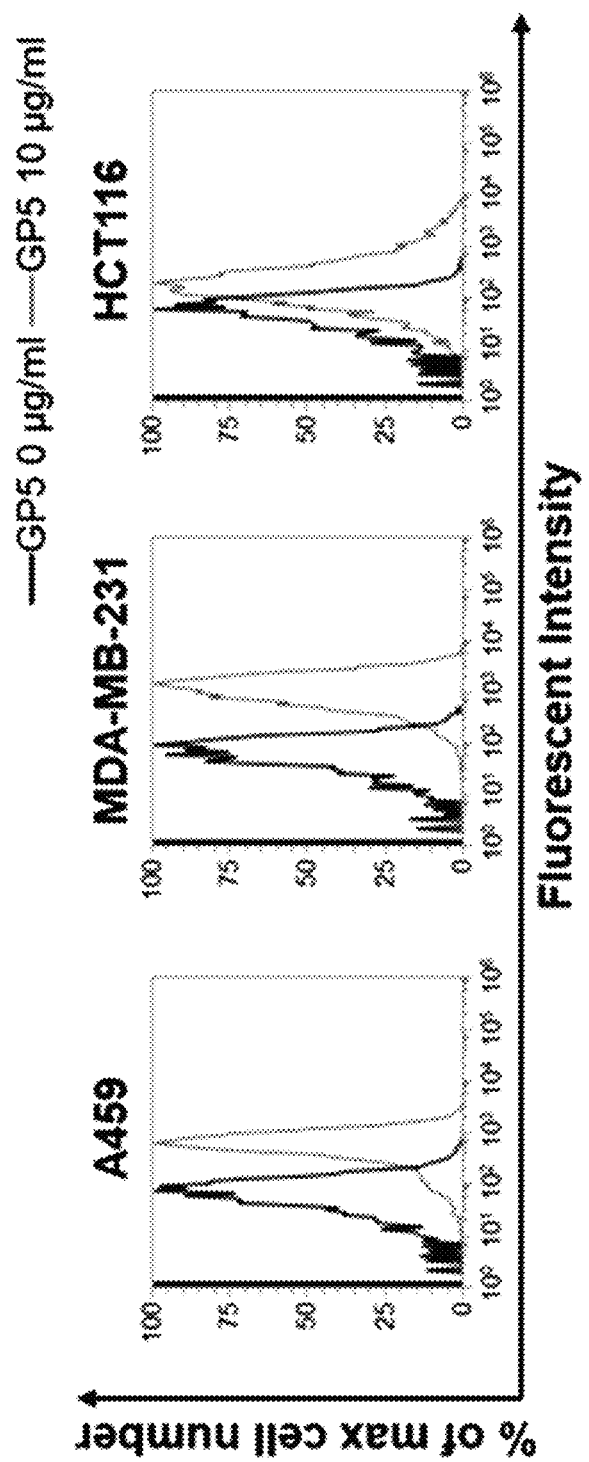
FIG. 4 confirms the expressions of beta 1 integrin on the surfaces of non-small cell lung cancer cell line A549, breast cancer cell line MDA-MB-231, and colorectal cancer cell line HCT116.

The flow cytometry analysis results revealed that beta 1 integrin was overexpressed on the cell surfaces of the non-small cell lung cancer cell line A549, the breast cancer cell line MDA-MB-231, and the colorectal cancer cell line HCT116 (FIG. 4).

<Example 5> Confirmation of Apoptotic Activity and Cell Growth Inhibitory Effect of Monoclonal Antibody GP5 in Cancer Cell Lines and Analysis of Anticancer Effect Mechanism The present inventors conducted an experiment to determine whether P5 and the inventive monoclonal antibody GP5 can induce apoptosis in various cancer cell lines, including a beta 1 integrin-expressing non-small cell lung cancer cell line.

Specifically, on the day before the experiment, each of non-small cell lung cancer cell line A549, breast cancer cell line MDA-MB-231, and colorectal cancer cell line HCT116 was plated on RPMI medium (WELGENE, Korea) supplemented with 10% bovine serum (GIBCO, USA) in a 24-well plate at a density of $5 \times 10^4$ cells/well in 1 ml medium and cultured at 37° C. and 5% $CO_2$ overnight.

On the next day, the supernatant was discarded and the RPMI medium (WELGENE, Korea) was treated with each of P5 and the monoclonal antibody GP5 until a concentration of 10 or 20 µg/ml was reached, followed by incubation at 37° C. and 5% $CO_2$ for 48 h. Fresh RPMI medium (WELGENE, Korea) was used as a negative control. After completion of the incubation, cells were washed with PBS, detached with 0.05% Trypsin-EDTA (Gibco, USA), placed in an EP tube, and washed again with PBS. Thereafter, cells were centrifuged at 3,500 rpm for 5 min. The cell pellets were collected and analyzed with an Attune NxT flow cytometer (ThermoFisher Scientific, USA) using an FITC Annexin V apoptosis detection kit with 7-AAD (BioLegend, USA). The results are shown in FIG. 5.

Figure 5A:
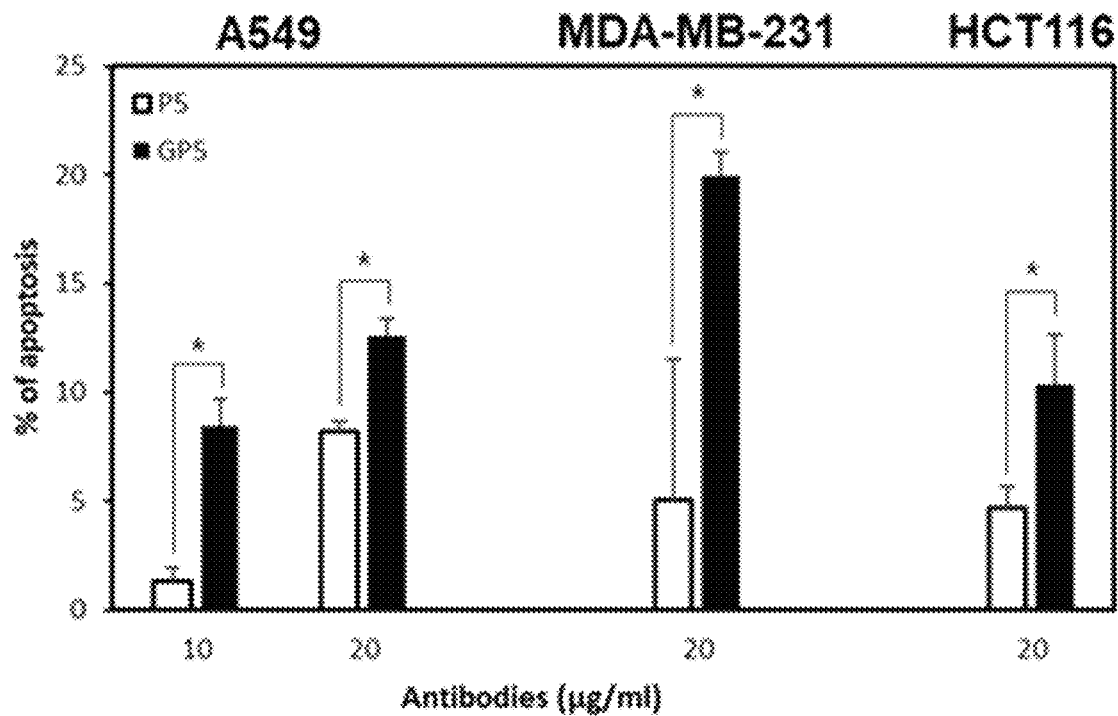
FIG. 5 shows the apoptotic activity of a monoclonal antibody (GP5) according to the present invention (FIG. 5A), the inhibitory activity of the monoclonal antibody GP5 for cell growth (FIG. 5B), and signaling pathways inhibited by the monoclonal antibody GP5 (FIG. 5C).

The inventive monoclonal antibody GP5 was found to have higher apoptotic activity than P5 and showed a concentration-dependent apoptotic effect in the non-small cell lung cancer cell line A549 (FIG. 5A).

The present inventors also conducted an experiment to determine whether the inventive monoclonal antibody GP5 can inhibit cell growth in various cancer cell lines, including a beta 1 integrin-expressing non-small cell lung cancer cell line.

Specifically, on the day before the experiment, each of non-small cell lung cancer cell line A549, breast cancer cell line MDA-MB-231, and colorectal cancer cell line HCT116 was plated on RPMI medium (WELGENE, Korea) supplemented with 10% bovine serum (GIBCO, USA) in a 12-well plate at a density of $1 \times 10^5$ cells/well in 1 ml medium and cultured at 37° C. and 5% $CO_2$ overnight.

On the next day, the supernatant was discarded and the RPMI medium (WELGENE, Korea) was treated with the monoclonal antibody GP5 until a concentration of 10, 20 or 50 µg/ml was reached, followed by incubation at 37° C. and 5% $CO_2$ for 48 h. Fresh RPMI medium (WELGENE, Korea) was used as a negative control. After completion of the incubation, cells were washed with PBS, treated with 200 µl of 4% paraformaldehyde (Biosesang, Korea) per well, and incubated at 4° C. for 10 min for their immobilization. The immobilized cells were washed with PBS and treated with 300 µl of 0.5% crystal violet (Sigma, USA) per well, followed by incubation in an orbital shaker for 30 min. After that, cells were washed with triple-distilled water until purple color did not appear in the washing solution. After drying, the dried plate was treated with 300 µl of 1% sodium dodecyl sulfate (Amresco, USA) per well to lyse the cells. Absorbance was measured at 570 nm using a spectrophotometer (Biotek, USA). The results are shown in FIG. 5B.

Figure 5B:
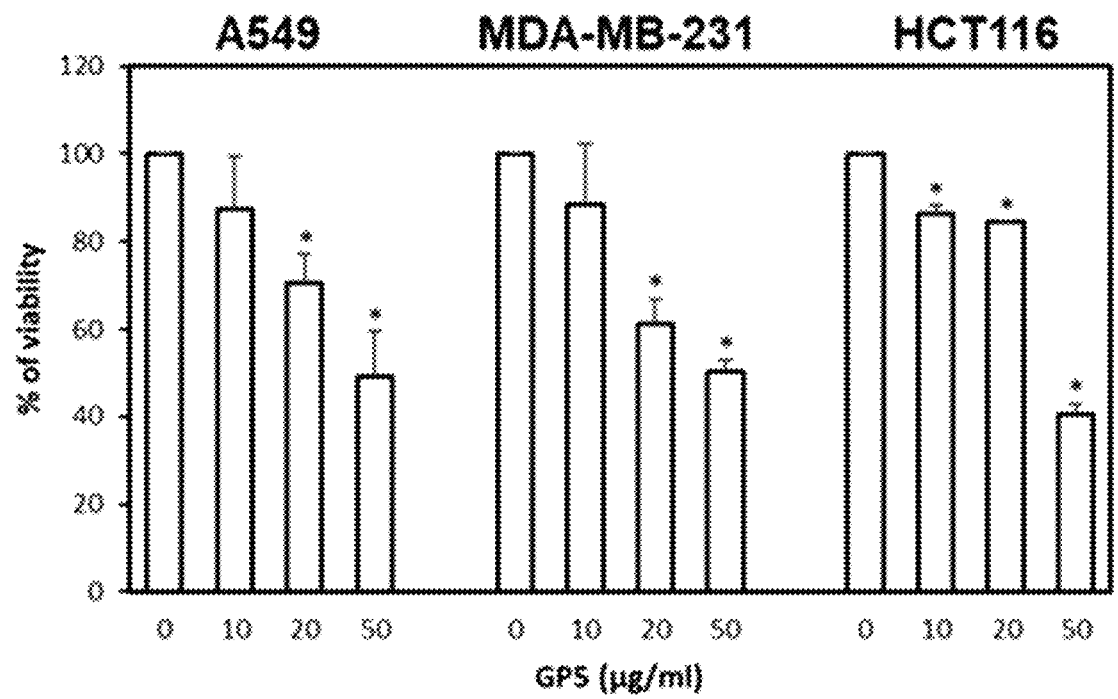

The inventive monoclonal antibody GP5 was found to have good inhibitory activity for cell growth and a concentration-dependent inhibitory effect on cell growth in the non-small cell lung cancer cell line A549, the breast cancer cell line MDA-MB-231, and the colorectal cancer cell line HCT116 (FIG. 5B).

The present inventors also conducted an experiment to investigate the anticancer mechanism of the monoclonal antibody GP5.

Figure 5C:
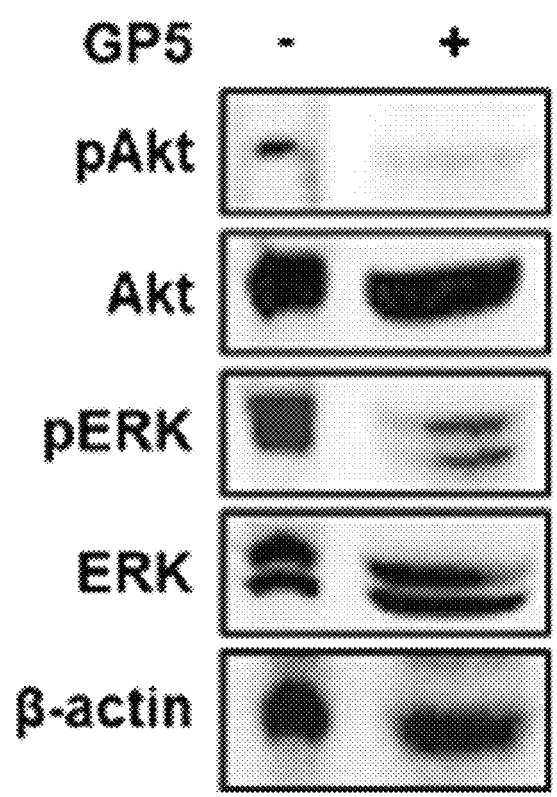

Beta 1 integrin is known to activate the Akt and ERK pathways involved in the survival and growth of cancer cells (Blandin A F, Renner G, Lehmann M, et al. β1 integrin as therapeutic targets to disrupt hallmarks of cancer. *Front Pharmacol*, 2015; 6:279.). Thus, the inhibitory activity of the monoclonal antibody GP5 on signaling pathways induced by beta 1 integrin was analyzed by immunoblotting. First, after A549 cell pellets were treated or untreated with the monoclonal antibody GP5 (20 µg/ml) for 48 h, Western blotting was performed according to the procedure described in the literature (Lee M S, Lee J C, Choi C Y et al. Production and characterization of monoclonal antibody to botulinum neurotoxin type B light chain by phage display. *Hybridoma (Larchmt)*, 2008; 27(1): 18-24). At this time, AKT, pAKT, ERK, pERK (1:1000 dilution; Cell Signaling Technology, USA) and β-actin (1:3000 dilution; Santa Cruz Biotechnology) antibodies were used as primary antibodies, and HRP-labeled anti-rabbit IgG (1:5000 dilution; Abcam, UK) or HRP-labeled anti-mouse IgG (1:5000 dilution; Abcam, UK) was used as a secondary antibody. The blots were visualized using an enhanced chemiluminescence system (ThermoFisher Scientific, USA) according to the manufacturer's guidelines. The results are shown in FIG. 5C. As shown in FIG. 5C, the expressions of pAKT and pERK were significantly reduced in A549 cells treated with the monoclonal antibody GP5.

In conclusion, the inventive monoclonal antibody GP5 has apoptotic and cell growth inhibitory activities due to its ability to inhibit the AKT and ERK pathways involved in the survival and growth of cancer cells activated by beta 1 integrin.

The above results reveal that the inventive monoclonal antibody GP5 has a therapeutic effect on various cancers, including non-small cell lung cancer. In addition, the superior apoptotic activity of the inventive monoclonal antibody GP5 compared to P5 demonstrates efficient modification of GP5.

<Example 6> Analysis of Internalization of Beta 1 Integrin on the Surface of Cancer Cells by the Monoclonal Antibody GP5

Figure 6A:
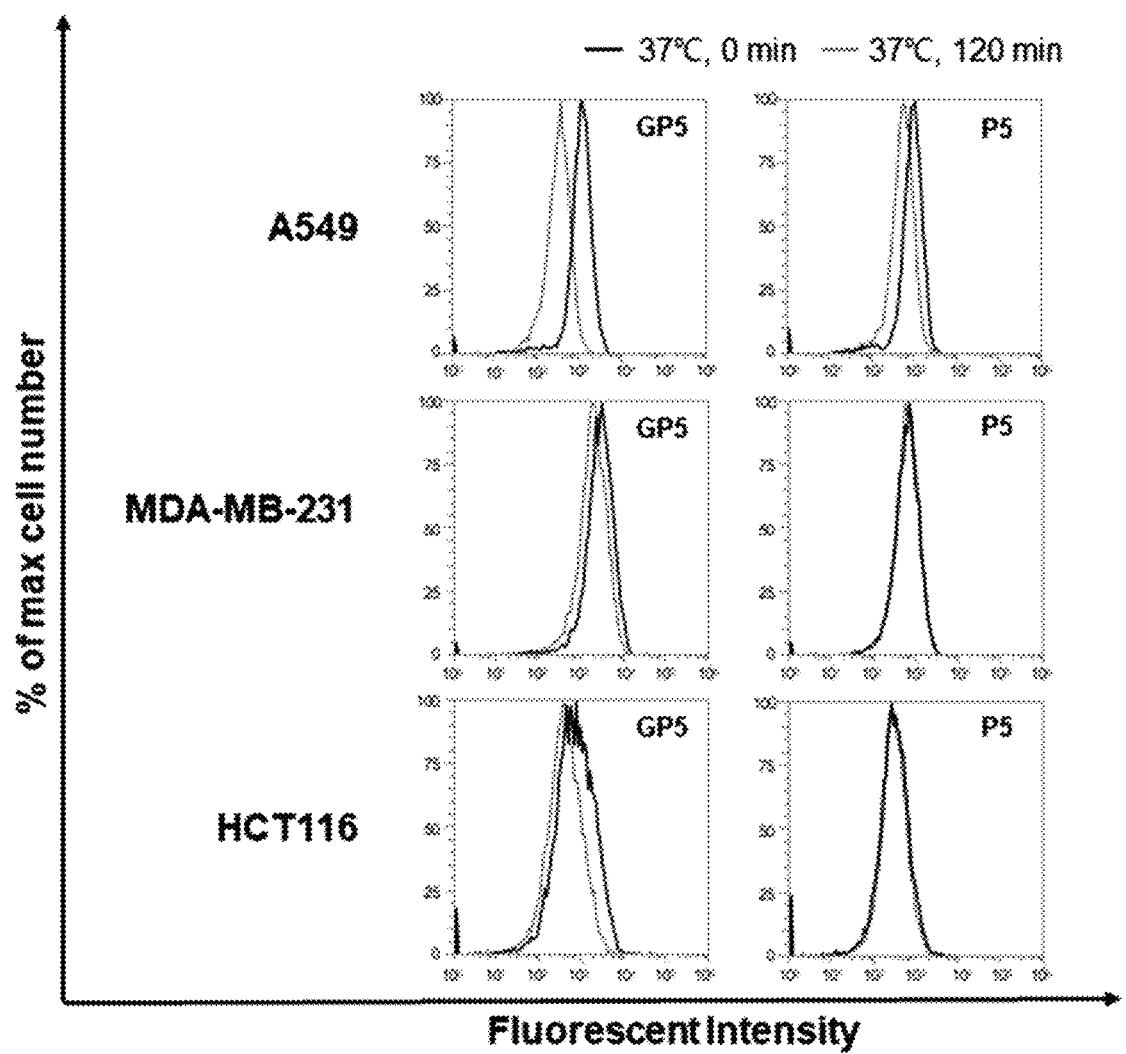
FIG. 6 confirms the induction of internalization of beta 1 integrin on the surface of cancer cells by a monoclonal antibody (GP5) of the present invention (FIG. 6A: 120 min.
FIG. 6B: time-dependent results in cell line A549).
Figure 6B:
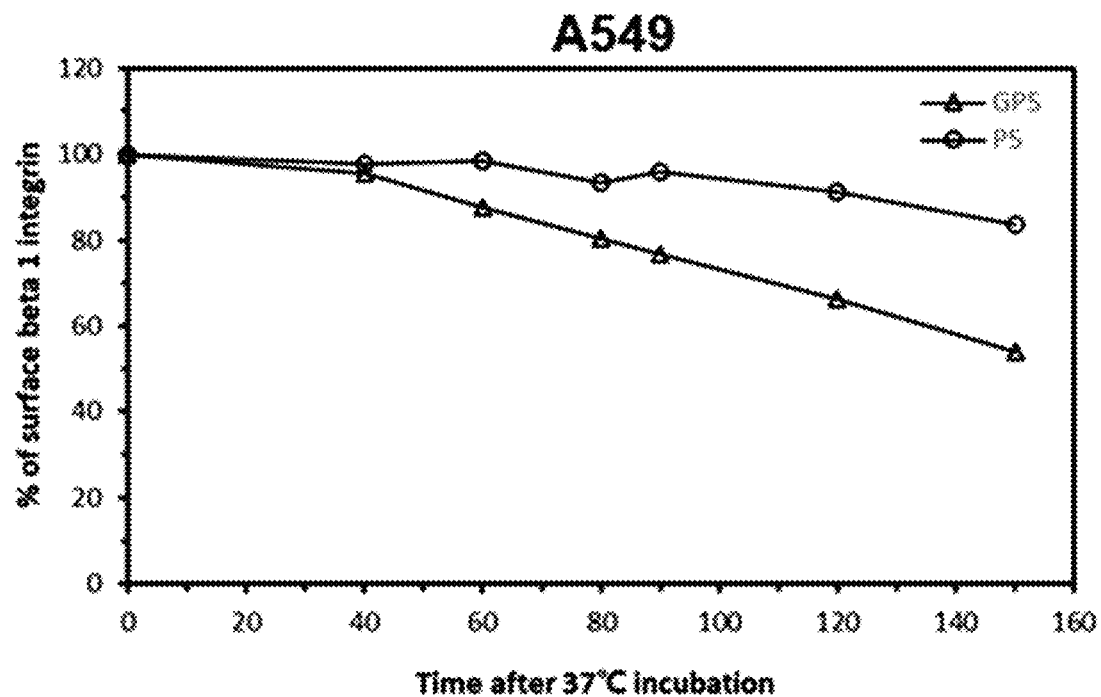

The present inventors conducted an experiment to evaluate the effects of P5 and the inventive monoclonal antibody GP5 on the induction of internalization of beta 1 integrin on the surface of various cancer cell lines, including a non-small cell lung cancer cell line. Specifically, $5 \times 10^5$ cells of each of non-small cell lung cancer cell line A549, breast cancer cell line MDA-MB-231, and colorectal cancer cell line HCT116 detached from T75 flasks (SPL, Korea) by treatment with 0.05% Trypsin-EDTA (Gibco, USA) ($5 \times 10^5$ cells) were placed in an EP tube, centrifuged at 3500 rpm for 5 min, and washed with PBS. Thereafter, the obtained cell pellets were treated with 100 µl of P5 or the monoclonal antibody GP5 diluted to 10 µg/ml in PBS. After incubation at 4° C. for 1 h, the non-small cell lung cancer cell line A549 continued to incubate at 37° C. for 0, 40, 60, 80, 90, 120, and 150 min and each of the breast cancer cell line MDA-MB-231 and the colorectal cancer cell line HCT116 continued to incubate at 37° C. for 120 min. After completion of the incubation, cells were washed with PBS and treated with 100 µl of FITC-labeled anti-mouse antibody (Sigma, USA) diluted 1:100 with PBS in the P5-treated EP tube or 100 µl of FITC-labeled anti-human antibody (Life technologies, USA) diluted 1:200 with PBS in the GP5-treated EP tube. Cells were incubated at 4° C. in the dark for 30 min, washed with PBS, and analyzed with an Attune NxT flow cytometer (ThermoFisher Scientific, USA). The results are shown in FIG. 6. Specifically, FIG. 6A shows the results of incubation of the non-small cell lung cancer cell line A549, the breast cancer cell line MDA-MB-231, and the colorectal cancer cell line HCT116 at 37° C. for 120 min and FIG. 6B shows the results of incubation of the non-small cell lung cancer cell line A549 with time after incubation at 37° C. Referring to FIG. 6, the proportions of surface beta 1 integrin on the A549, MDA-MB-231 and HCT116 cells treated with the monoclonal antibody GP5 were significantly reduced compared to those of surface beta 1 integrin on the A549, MDA-MB-231 and HCT116 cells treated with P5.

These results indicate that the binding of the monoclonal antibody GP5 to beta 1 integrin induces internalization of beta 1 integrin and suggest that the monoclonal antibody GP5 can bind to and be internalized in beta 1 integrin overexpressing cells as well as non-small cell lung cancer cells. This internalization effect is attributed to the modification of the inventive antibody and explains the superior anticancer activity of the monoclonal antibody GP5 compared to P5.

<Example 7> Analysis of Apoptosis in Gefitinib-Resistant Cell Lines by the Monoclonal Antibody GP5

Beta 1 integrin is known to cause resistance to cytotoxic chemotherapy in a variety of cancers (Park C C et al. Cancer Res, 2006, 66(3): 1526-35). Thus, the present inventors conducted an experiment to determine the degrees of apoptosis induction in a non-small cell lung cancer cell line resistant to gefitinib used in cytotoxic chemotherapy when the monoclonal antibody GP5 was used alone or in combination with gefitinib.

First, the expressions of beta 1 integrin in gefitinib-resistant non-small cell lung cancer cell line PC9GR and parental non-small cell lung cancer cell line PC9 were confirmed in the same manner as in Example 4.

Figure 7A:
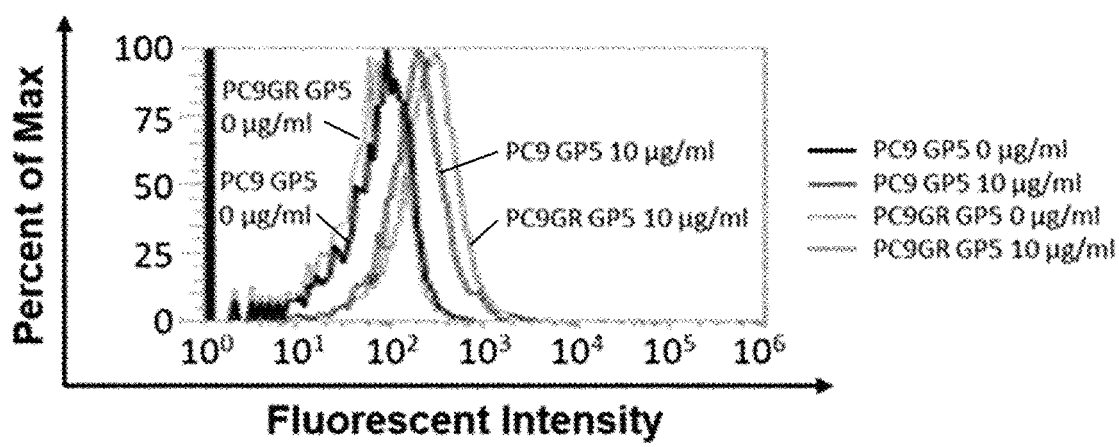
FIG. 7 shows an improvement in the sensitivity to gefitinib in PC9GR, a gefitinib-resistant non-small cell lung cancer cell line, to a level in parental PC9 cells when a monoclonal antibody (GP5) of the present invention was used in combination with gefitinib (FIG. 7A confirms the expressions of beta 1 integrin on the surfaces of PC9 and PC9GR.
FIG. 7B confirms the degrees of apoptosis in PC9 and PC9GR induced by a combination of gefitinib and the monoclonal antibody GP5).

The flow cytometry analysis revealed that the peak corresponding to the binding of the monoclonal antibody GP5 to beta 1 integrin in the gefitinib-resistant non-small cell lung cancer cell line PC9GR more shifted to the right than that in the parental non-small cell lung cancer cell line PC9, demonstrating that beta 1 integrin was more expressed in PC9GR than in the parental PC9 (FIG. 7A).

The abilities of the monoclonal antibody GP5 or a combination thereof with gefitinib to induce apoptosis in the cell lines PC9 and PC9GR were investigated. Specifically, on the day before the experiment, each of cell lines PC9 and PC9GR was plated on RPMI medium (WELGENE, Korea) supplemented with 10% bovine serum (GIBCO, USA) in a 12-well plate at a density of $1 \times 10^5$ cells/well in 1 ml medium and cultured at 37° C. and 5% $CO_2$ overnight.

Figure 7B:
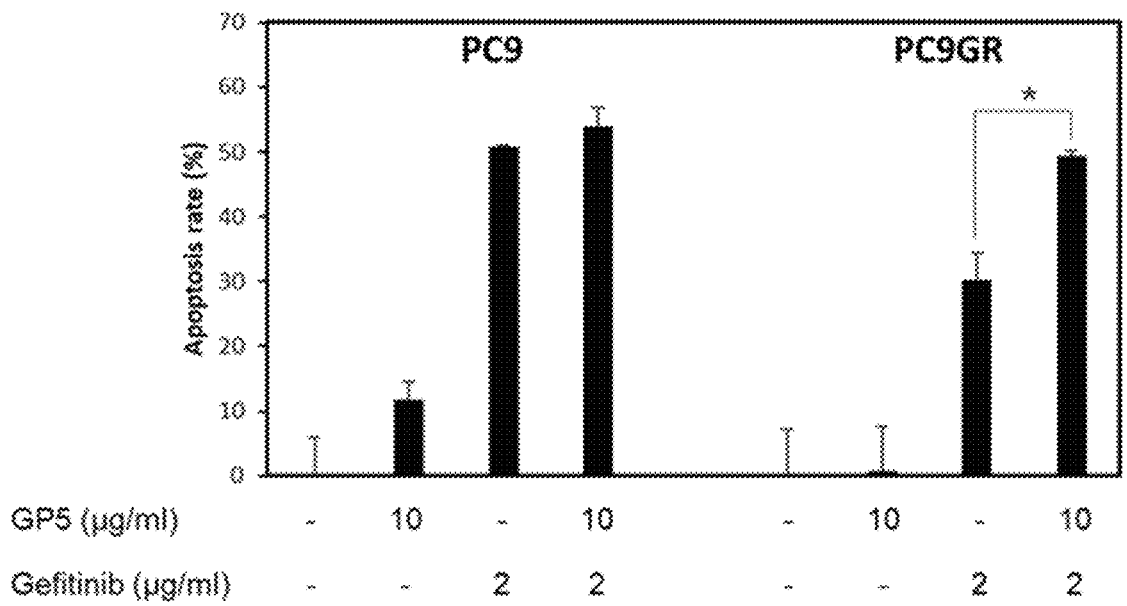

On the next day, the supernatant was discarded and the RPMI medium (WELGENE, Korea) was treated with gefitinib (Sigma, USA) and/or the monoclonal antibody GP5 until a concentration of 2 (gefitinib) or 10 µg/ml (GP5) was reached, followed by incubation at 37° C. and 5% $CO_2$ for 24 h. Fresh RPMI medium (WELGENE, Korea) was used as a negative control. After completion of the incubation, cells were washed with PBS, detached with 0.05% Trypsin-EDTA (Gibco, USA), placed in an EP tube, and washed again with PBS. Thereafter, cells were centrifuged at 3,500 rpm for 5 min. The cell pellets were collected and analyzed with an Attune NxT flow cytometer (ThermoFisher Scientific, USA) using an FITC Annexin V apoptosis detection kit with 7-AAD (BioLegend, USA). The results are shown in FIG. 7B. As shown in FIG. 7B, gefitinib induced high apoptosis (>50%) in the parental PC9 cells but lower apoptosis (~30%) in PC9GR. The combination of the monoclonal antibody GP5 and gefitinib induced high apoptosis (~50%) in PC9GR.

The sensitivity to gefitinib was found to be lower in the gefitinib-resistant cell line PC9GR than in the parental PC9. The lowered sensitivity to gefitinib in PC9GR was restored to the level in the cell line PC9 when the combination of gefitinib and the monoclonal antibody GP5 was used (FIG. 7B).

Based on these results, it was concluded that the inventive monoclonal antibody GP5 can suppress resistance to anticancer drugs due to its ability to block beta 1 integrin, which is a cause of resistance to anticancer drugs.

<Example 8> Analysis of Anticancer Activity of the Monoclonal Antibody GP5 in Human A549 Non-Small Cell Lung Cancer Xenograft Model The present inventors conducted an experiment to determine whether P5 and the inventive monoclonal antibody GP5 exhibit anticancer activities in nude mice xenografted with a non-small cell lung cancer cell line.

Figure 8A:
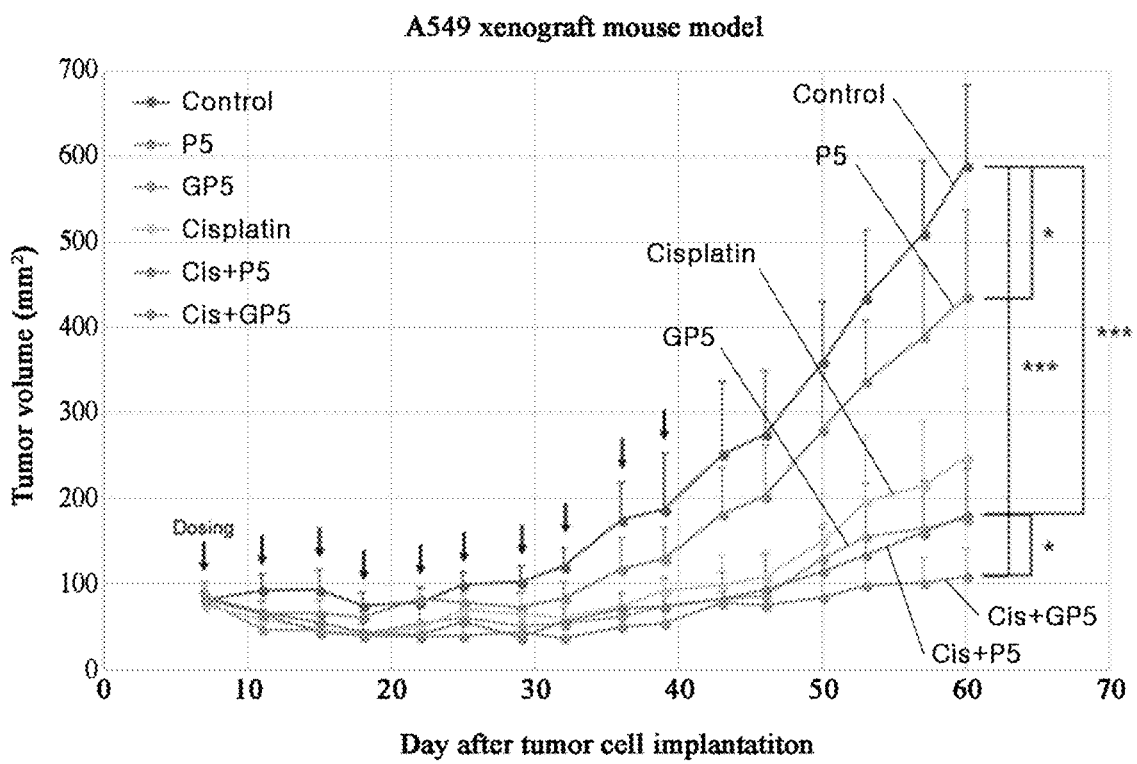
FIG. 8 shows the anticancer activity of an antibody (GP5) according to the present invention in a mouse model xenografted with a non-small cell lung cancer cell line (FIG. 8A: comparison of tumor volumes.
FIG. 8B: comparison of tumor sizes).

Specifically, non-small cell lung cancer cell line A549 was inoculated subcutaneously into the flanks of female Balb/c nude mice (SLC, Japan) at $5 \times 10^6$ cells/mouse. Mice were weighed twice a week and the tumor volume was calculated by using the formula: V=width×width×length/2. When the tumor volume reached ~80 $mm^3$ 7 days after inoculation, mice were divided randomly, 6 animals per group. PBS (negative control), P5 or the monoclonal antibody GP5 at a dose of 1 mg/kg or cisplatin (Sigma, USA) at a dose of 2.5 mg/kg was administered intraperitoneally to mice twice a week for 5 weeks. For a combined treatment group, 1 mg/kg of P5 or the monoclonal antibody GP5 and 2.5 mg/kg of cisplatin (Sigma, USA) were administered to mice twice a week for 5 weeks. Thereafter, the tumor size and weight were measured twice a week for 3 weeks without antibody and cisplatin administration. The tumor volume was calculated for each drug administration. The results are shown in FIG. 8A (see the arrows (↓): time points of administration, *: P<0.05 compared to the negative control using the Student's t-test, *: P<0.001 compared to the negative control using the Student's t-test). Mice were sacrificed and cancer tissues were excised for the subsequent example 9. FIG. 8**B shows images of the excised cancer tissues.

Figure 8B:
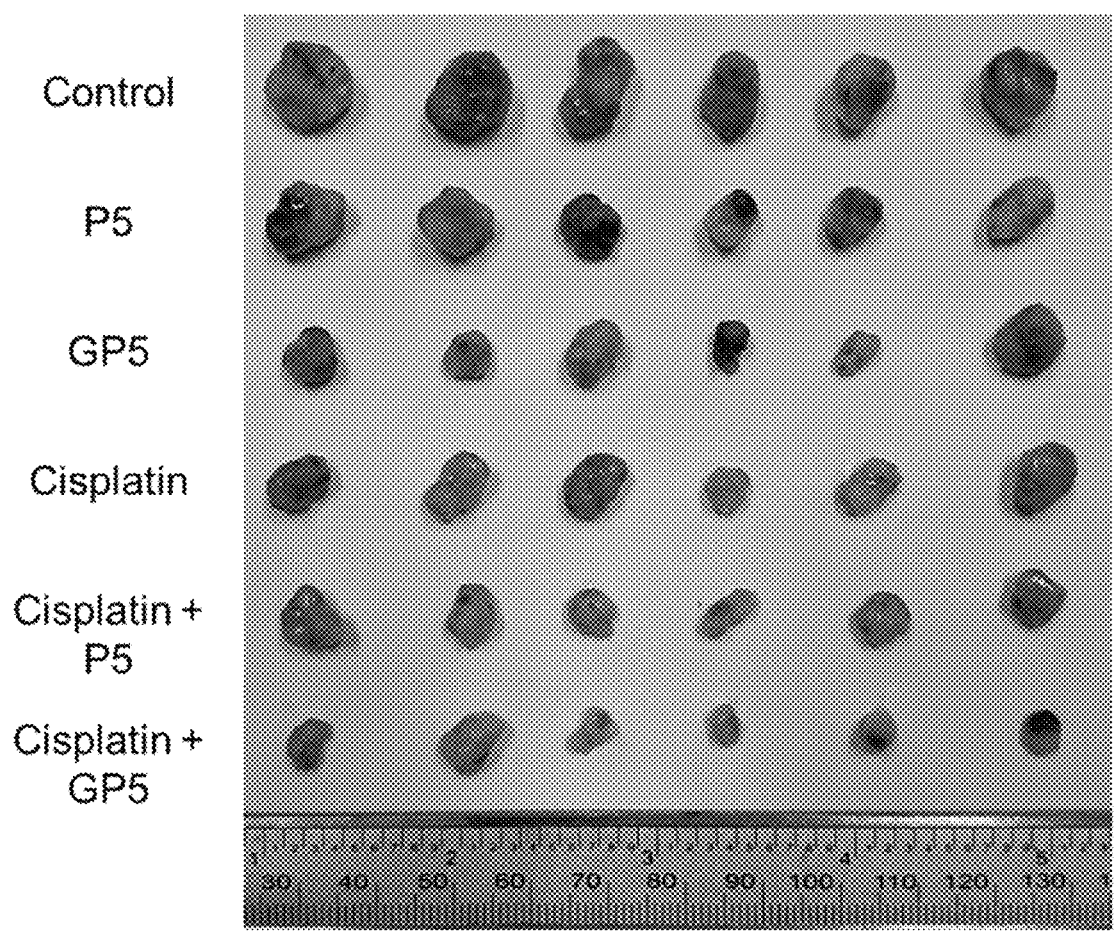

As shown in FIGS. 8a and 8b, the inventive monoclonal antibody GP5 was found to have superior anticancer activity compared to P5 when administered alone and showed higher anticancer activity than cisplatin, which is known as a therapeutic drug for non-small cell lung cancer. In addition, combined administration of the monoclonal antibody GP5 and cisplatin produced superior anticancer activity compared to single administration of the monoclonal antibody GP5. The tumor volume did not increase even after the drug administration was stopped. That is, both single and combined administration of the monoclonal antibody GP5 led to an increase in anticancer efficacy compared to the single administration of P5 or cisplatin.

<Example 9> Histopathological Studies Based on Immunohistochemistry

Immunohistochemical staining was performed in the LOGONE Bio-Convergence Research Foundation (Korea) and histopathological analysis was performed in SG Medical Inc (Korea). At the end of the experiment (Day 60), all mice were sacrificed for tissue processing, immunohistochemical staining, and histological analysis. The experimental animals were subjected to laparotomy under deep anesthesia and blood was collected from the heart. Thereafter, tissues were excised, fixed in 4% formaldehyde solution, embedded in paraffin, and sectioned to a thickness of 4 µm at the largest tumor area. The paraffin was removed, followed by rehydration. For immunoperoxidase labeling, intracellular peroxidase was inhibited by exposure to 0.3% $H_2O_2$ for 15 min. Then, the sections were placed in an antigen retrieval solution (TE pH 9.0) (Sigma, USA) for antigen retrieval, heated in a pressure cooker (Bio SB, USA) for 30 min, and exposed to a blocking solution for 20 min to exclude non-specific immune responses.

Figure 9A:
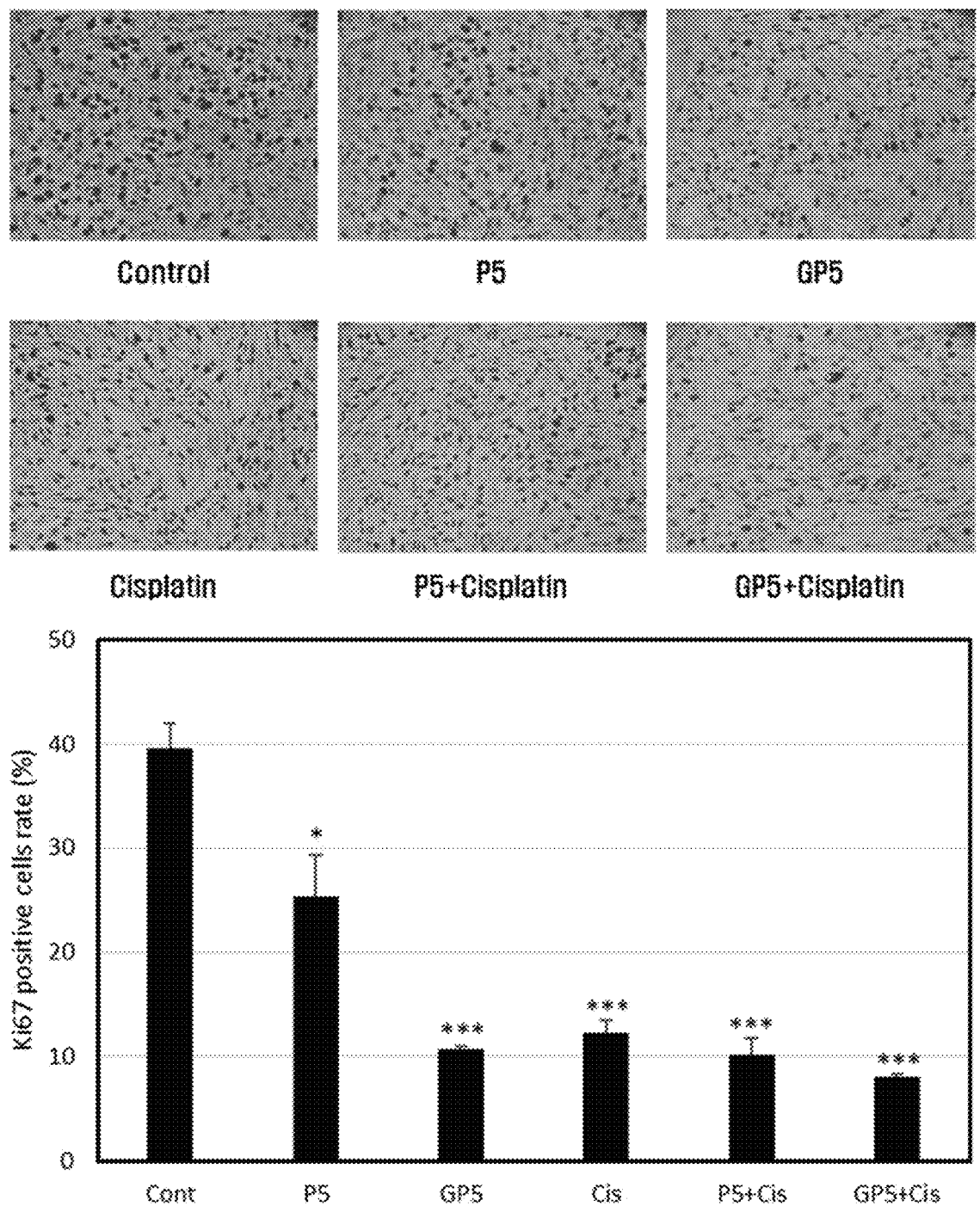
FIG. 9 shows the inhibitory activity of an antibody (GP5) according to the present invention for the proliferation of tumor cells (FIG. 9A), the inhibitory activity of the antibody (GP5) for intratumoral angiogenesis (FIG. 9B), and the ability of the antibody (GP5) to induce tumor apoptosis (FIG. 9C).

Immunohistochemical staining of human Ki67 was performed using a primary rabbit antibody to human Ki67 (Abcam, UK) to evaluate the degree of tumor cell proliferation. The primary antibody was diluted and incubated on the tissue section treated with the blocking solution at room temperature for 1 h to form an antigen-antibody complex. The antigen-antibody complex was conjugated with an HRP-labeled secondary antibody (EnVision+ System-HRP labeled polymer anti-rabbit (Dako, USA)) and allowed to develop color using 3,3'-diaminobenzidine (DAB) as a substrate with a liquid DAB+ substrate chromogen system (Dako, USA). Hematoxylin (Sigma, USA) staining was used as a counterstaining for the DAB staining. Images were observed using an optical microscope (ix71, Olympus, Japan). The proportions of the Ki67 stained sites were calculated using ImageJ software (NIH, USA). The results are shown in FIG. 9A (*: P<0.05 compared to the negative control using the Student's t-test, ***: P<0.001 compared to the negative control using the Student's t-test).

Figure 9B:
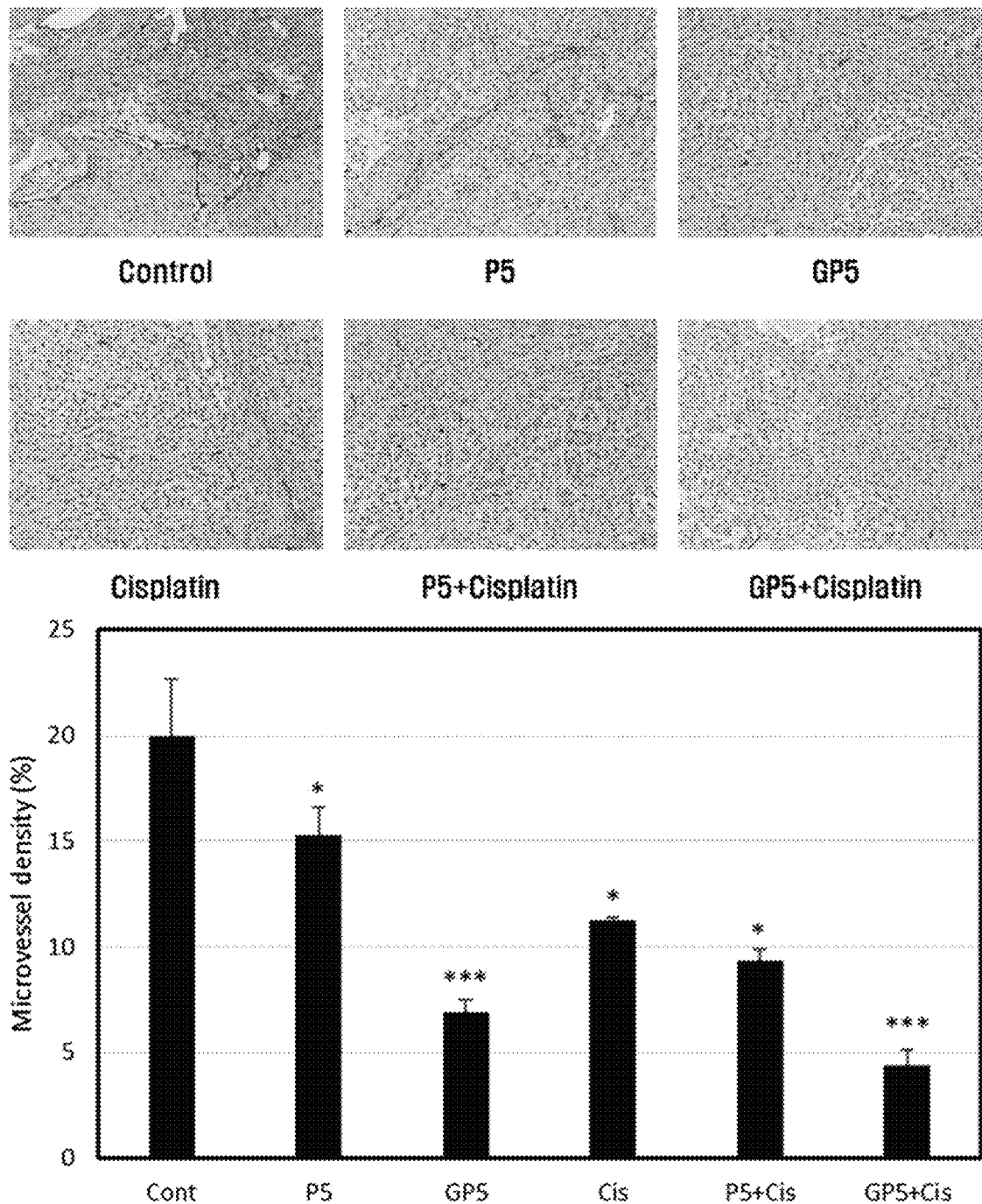

Immunohistochemical staining of mouse CD31 was performed using a primary rabbit antibody to CD31 (Abcam, UK) to evaluate changes in tumor blood vessels. The immunohistochemical staining was performed in the same manner as described above for Ki67 staining. Images were observed using an optical microscope (ix71, Olympus, Japan). The proportions of the CD31 stained sites were calculated using ImageJ software (NIH, USA). The results are shown in FIG. 9B (*: P<0.05 compared to the negative control using the Student's t-test, ***: P<0.001 compared to the negative control using the Student's t-test).

Figure 9C:
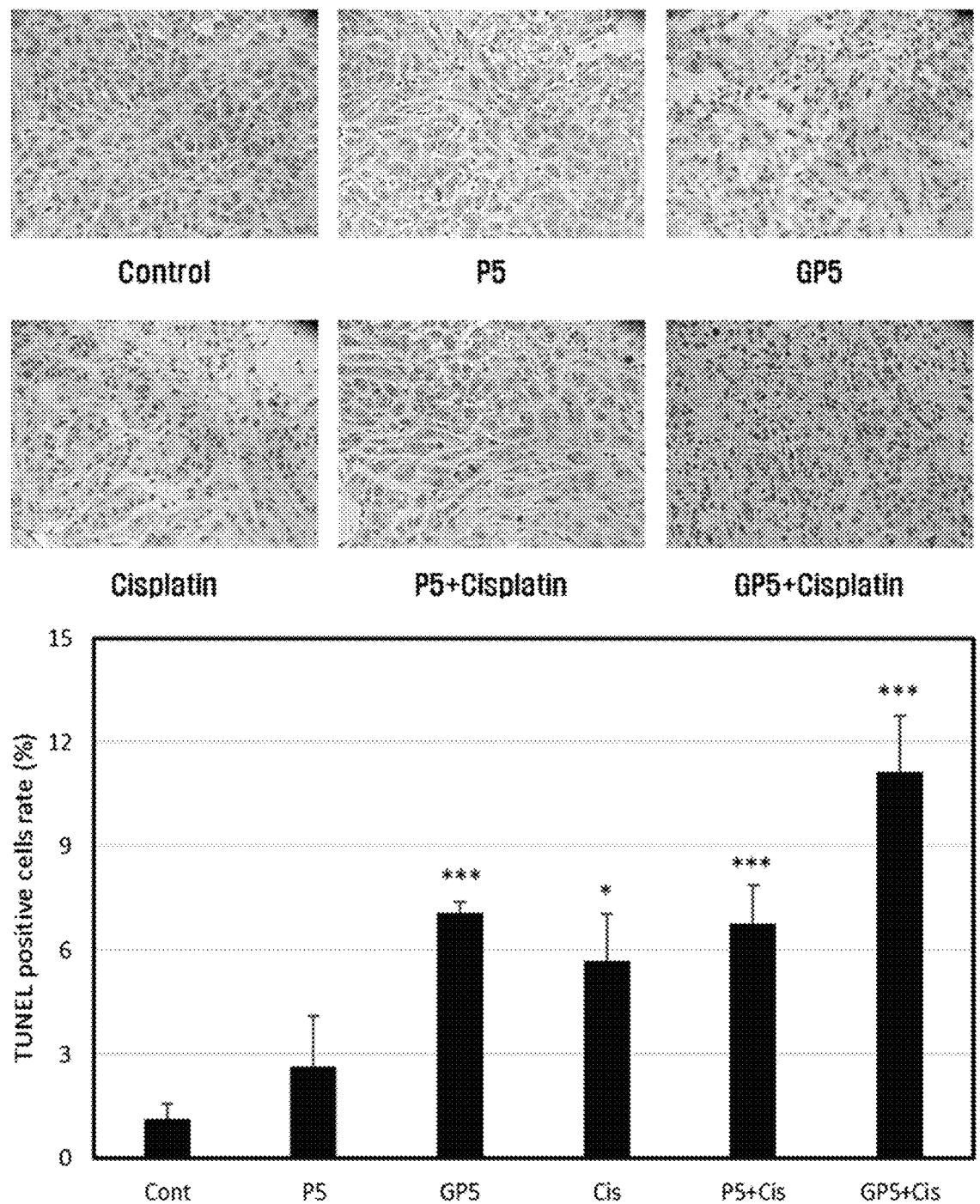

Terminal deoxynucleotidyl transferase (dUTP) nick-end labeling (TUNEL) staining was performed using an ApopTag peroxidase in situ apoptosis detection kit (Chemicon, USA) to evaluate the degree of tumor apoptosis. Color development was performed with a liquid DAB+ substrate chromogen system (Dako, USA). Hematoxylin staining was performed as a counterstaining for the DAB staining. Images were observed using an optical microscope (ix71, Olympus, Japan). The proportions of the apoptotic sites were calculated using ImageJ software (NIH, USA). The results are shown in FIG. 9C (*: P<0.05 compared to the negative control using the Student's t-test).

As a result of the immunohistochemical staining, the expressions of Ki67 and CD31 were the highest in the negative control (FIGS. 9a and 9b) and almost no TUNEL-stained cells were observed (FIG. 9C), indicating active proliferation and angiogenesis of cancer cells in the negative control. The expressions of Ki67 and CD31 were lower in the group administered with the monoclonal antibody GP5 alone than in the group administered with the monoclonal antibody P5 (FIGS. 9a and 9b). A larger number of TUNEL-stained cells were observed in the group administered with the monoclonal antibody GP5 alone than in the group administered with the monoclonal antibody P5 (FIG. 9C). These results indicate that the monoclonal antibody GP5 is effective in inhibiting cancer cell proliferation and angiogenesis and inducing apoptosis compared to P5. This effect was more pronounced when the monoclonal antibody GP5 and cisplatin were co-administered than when administered alone (FIGS. 9a, 9b, and 9c). These results indicate that the monoclonal antibody GP5 possesses anticancer activity due to its ability to inhibit cancer cell proliferation and angiogenesis and induce apoptosis and maximizes this activity when combined with cisplatin.

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

We claim:

1. A monoclonal antibody or fragment thereof that recognizes and binds specifically to beta 1 integrin as an antigen wherein the monoclonal antibody or fragment thereof comprises replaced amino acids at the following positions according to the Kabat EU numbering system:
   a) the heavy chain variable region (VH) SEQ ID NO: 1 with substitutions A9S, I20V, T25S, S30T, K67R, S76T, N77D, and Q82E; and
   b) the light chain variable region (VL) SEQ ID NO: 2 with substitutions V11L, F41Y, and R44K.

2. The monoclonal antibody or fragment thereof according to claim 1, wherein the monoclonal antibody or fragment thereof comprises a heavy chain variable region having the sequence set forth in SEQ ID NO: 3 and a light chain variable region having the sequence set forth in SEQ ID NO: 4.

3. The monoclonal antibody or fragment thereof according to claim 1, wherein the monoclonal antibody or fragment thereof is a single-chain variable fragment (scFv).

4. A multispecific antibody or antibody-drug conjugate (ADC) comprising the monoclonal antibody or fragment thereof according to claim 1.

5. A nucleic acid molecule encoding the monoclonal antibody or fragment thereof according to claim 1.

6. A vector comprising the nucleic acid molecule according to claim 5.

7. A host cell comprising the vector according to claim 6.

8. A method for treating cancer comprising administering a pharmaceutical composition comprising the monoclonal antibody or fragment thereof according to claim 1, a nucleic acid molecule encoding the monoclonal antibody or fragment thereof, or a vector comprising the nucleic acid molecule.

9. The method according to claim 8, wherein the cancer is resistant to cytotoxic chemotherapy.

10. The method according to claim 8, wherein the cancer is lung cancer, breast cancer or colon cancer.

11. A method for quantifying beta 1 integrin in a sample, comprising treating the sample with the monoclonal antibody or fragment thereof according to claim 1.

12. A method for providing information for the diagnosis of a disease caused by overexpression of beta 1 integrin, comprising (a) separating a sample from a subject, (b) treating the sample with the monoclonal antibody or fragment thereof according to claim 1, and (c) determining whether the expression level of beta 1 integrin in the sample from the subject is higher than that of beta 1 integrin in a normal sample.

13. The method according to claim 12, wherein the disease caused by overexpression of beta 1 integrin is a cancer.

14. A kit for quantifying beta 1 integrin comprising the monoclonal antibody or fragment thereof according to claim 1.

* * * * *

SEQUENCE LISTING

```
<160> NUMBER OF SEQ ID NOS: 32

<210> SEQ ID NO 1
<211> LENGTH: 118
<212> TYPE: PRT
<213> ORGANISM: Artificial Sequence
<220> FEATURE:
<223> OTHER INFORMATION: P5 - heavy chain variable region

<400> SEQUENCE: 1

Gln Val Gln Leu Gln Gln Ser Gly Ala Glu Leu Met Lys Pro Gly Ala
```

```
                1               5                  10                 15
            Ser Val Lys Ile Ser Cys Lys Ala Thr Gly Tyr Thr Phe Ser Asn Tyr
                            20                 25                 30

Trp Ile Glu Trp Ile Val Gln Arg Pro Gly His Gly Leu Glu Trp Ile
                            35                 40                 45

Gly Glu Ile Leu Pro Gly Ser Val Asn Thr Asn Tyr Asn Ala Lys Phe
                        50                 55                 60

Lys Asp Lys Ala Thr Phe Thr Ala Asp Thr Ser Ser Asn Thr Ala Ser
            65                 70                 75                 80

Met Gln Leu Ser Ser Leu Thr Ser Glu Asp Ser Ala Val Tyr Tyr Cys
                            85                 90                 95

Ala Leu Ala Thr Pro Tyr Tyr Ala Leu Asp Ser Trp Gly Gln Gly Thr
                            100                105                110

Ser Val Thr Val Ser Ser
                        115

<210> SEQ ID NO 2
<211> LENGTH: 112
<212> TYPE: PRT
<213> ORGANISM: Artificial Sequence
<220> FEATURE:
<223> OTHER INFORMATION: P5 - light chain variable region

<400> SEQUENCE: 2

Asp Ile Val Met Thr Gln Ala Ala Pro Ser Val Ser Val Thr Pro Gly
1               5                  10                 15

Glu Ser Val Ser Ile Ser Cys Arg Ser Thr Glu Ser Leu Leu His Ser
                20                 25                 30

Asn Gly Asn Thr Tyr Leu Tyr Trp Phe Leu Gln Arg Pro Gly Gln Ser
            35                 40                 45

Pro Gln Leu Leu Ile Tyr Arg Met Ser Asn Arg Ala Ser Gly Val Pro
        50                 55                 60

Asp Arg Phe Ser Gly Ser Gly Ser Gly Thr Ala Phe Thr Leu Lys Ile
65                 70                 75                 80

Arg Arg Val Glu Ala Glu Asp Val Gly Val Tyr Tyr Cys Met Gln His
                85                 90                 95

Leu Glu Tyr Pro Phe Thr Phe Gly Ala Gly Thr Lys Leu Glu Leu Lys
                100                105                110

<210> SEQ ID NO 3
<211> LENGTH: 118
<212> TYPE: PRT
<213> ORGANISM: Artificial Sequence
<220> FEATURE:
<223> OTHER INFORMATION: GP5 - heavy chain variable region

<400> SEQUENCE: 3

Gln Val Gln Leu Gln Gln Ser Gly Ser Glu Leu Met Lys Pro Gly Ala
1               5                  10                 15

Ser Val Lys Val Ser Cys Lys Ala Ser Gly Tyr Thr Phe Thr Asn Tyr
                20                 25                 30

Trp Ile Glu Trp Ile Val Gln Arg Pro Gly His Gly Leu Glu Trp Ile
            35                 40                 45

Gly Glu Ile Leu Pro Gly Ser Val Asn Thr Asn Tyr Asn Ala Lys Phe
        50                 55                 60

Lys Asp Arg Ala Thr Phe Thr Ala Asp Thr Ser Thr Asp Thr Ala Ser
65                 70                 75                 80
```

```
Met Glu Leu Ser Ser Leu Thr Ser Glu Asp Ser Ala Val Tyr Tyr Cys
             85                  90                  95

Ala Leu Ala Thr Pro Tyr Tyr Ala Leu Asp Ser Trp Gly Gln Gly Thr
            100                 105                 110

Ser Val Thr Val Ser Ser
            115

<210> SEQ ID NO 4
<211> LENGTH: 112
<212> TYPE: PRT
<213> ORGANISM: Artificial Sequence
<220> FEATURE:
<223> OTHER INFORMATION: GP5 - light chain variable region

<400> SEQUENCE: 4

Asp Ile Val Met Thr Gln Ala Ala Pro Ser Leu Ser Val Thr Pro Gly
1               5                   10                  15

Glu Ser Val Ser Ile Ser Cys Arg Ser Thr Glu Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Arg Ala Ser Gly Val Pro
    50                  55                  60

Asp Arg Phe Ser Gly Ser Gly Ser Gly Thr Ala Phe Thr Leu Lys Ile
65                  70                  75                  80

Arg Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

<210> SEQ ID NO 5
<211> LENGTH: 63
<212> TYPE: DNA
<213> ORGANISM: Artificial Sequence
<220> FEATURE:
<223> OTHER INFORMATION: VH forward primer 1

<400> SEQUENCE: 5
cagaattcac tctaaccatg gaatggagct gggtctttct cttcttcctg tcagtaacta      60
cag                                                                   63

<210> SEQ ID NO 6
<211> LENGTH: 51
<212> TYPE: DNA
<213> ORGANISM: Artificial Sequence
<220> FEATURE:
<223> OTHER INFORMATION: VH forward primer 2

<400> SEQUENCE: 6
cttcctgtca gtaactacag gtgtccactc ccaggtgcaa ctgcagcagt c               51

<210> SEQ ID NO 7
<211> LENGTH: 39
<212> TYPE: DNA
<213> ORGANISM: Artificial Sequence
<220> FEATURE:
<223> OTHER INFORMATION: VH reverse primer 1

<400> SEQUENCE: 7
ccagcgtgac cgtatccagc gcctccacca agggcccca                            39
```

<210> SEQ ID NO 8
<211> LENGTH: 39
<212> TYPE: DNA
<213> ORGANISM: Artificial Sequence
<220> FEATURE:
<223> OTHER INFORMATION: VH reverse primer 2

<400> SEQUENCE: 8
ccagcgtgac cgtatccagc gcctccacca agggcccca                    39

<210> SEQ ID NO 9
<211> LENGTH: 37
<212> TYPE: DNA
<213> ORGANISM: Artificial Sequence
<220> FEATURE:
<223> OTHER INFORMATION: CH forward primer 1

<400> SEQUENCE: 9
gggcccttgg tggaggcgct ggatacggtc acgctgg                      37

<210> SEQ ID NO 10
<211> LENGTH: 20
<212> TYPE: DNA
<213> ORGANISM: Artificial Sequence
<220> FEATURE:
<223> OTHER INFORMATION: CH reverse primer 1

<400> SEQUENCE: 10
gcattgtctg agtaggtgtc                                         20

<210> SEQ ID NO 11
<211> LENGTH: 63
<212> TYPE: DNA
<213> ORGANISM: Artificial Sequence
<220> FEATURE:
<223> OTHER INFORMATION: HC forward primer 1

<400> SEQUENCE: 11
cagaattcac tctaaccatg gaatggagct gggtctttct cttcttcctg tcagtaacta   60
cag                                                            63

<210> SEQ ID NO 12
<211> LENGTH: 20
<212> TYPE: DNA
<213> ORGANISM: Artificial Sequence
<220> FEATURE:
<223> OTHER INFORMATION: HC reverse primer 1

<400> SEQUENCE: 12
gcattgtctg agtaggtgtc                                         20

<210> SEQ ID NO 13
<211> LENGTH: 68
<212> TYPE: DNA
<213> ORGANISM: Artificial Sequence
<220> FEATURE:
<223> OTHER INFORMATION: VL forward primer 1

<400> SEQUENCE: 13
aagcttcggc acgagcagac cagcatgggc atcaagatgg agacacattc tcaggtcttt   60
gtatacat                                                       68

<210> SEQ ID NO 14
<211> LENGTH: 68
<212> TYPE: DNA

```
<213> ORGANISM: Artificial Sequence
<220> FEATURE:
<223> OTHER INFORMATION: VL forward primer 2

<400> SEQUENCE: 14
tctcaggtct tgtatacat gttgctgtgg ttgtctggtg ttgaaggaga tattgtgatg    60
actcaggc                                                            68

<210> SEQ ID NO 15
<211> LENGTH: 28
<212> TYPE: DNA
<213> ORGANISM: Artificial Sequence
<220> FEATURE:
<223> OTHER INFORMATION: VL reverse primer 1

<400> SEQUENCE: 15
ggaccaagct ggagctgaaa cgtacggt                                      28

<210> SEQ ID NO 16
<211> LENGTH: 28
<212> TYPE: DNA
<213> ORGANISM: Artificial Sequence
<220> FEATURE:
<223> OTHER INFORMATION: VL reverse primer 2

<400> SEQUENCE: 16
ggaccaagct ggagctgaaa cgtacggt                                      28

<210> SEQ ID NO 17
<211> LENGTH: 39
<212> TYPE: DNA
<213> ORGANISM: Artificial Sequence
<220> FEATURE:
<223> OTHER INFORMATION: Ck forward primer 1

<400> SEQUENCE: 17
tggggccctt ggtggaggcg ctggatacgg tcacgctgg                          39

<210> SEQ ID NO 18
<211> LENGTH: 22
<212> TYPE: DNA
<213> ORGANISM: Artificial Sequence
<220> FEATURE:
<223> OTHER INFORMATION: Ck reverse primer 1

<400> SEQUENCE: 18
cattttgtct gactaggtgt cc                                            22

<210> SEQ ID NO 19
<211> LENGTH: 68
<212> TYPE: DNA
<213> ORGANISM: Artificial Sequence
<220> FEATURE:
<223> OTHER INFORMATION: LC forward primer 1

<400> SEQUENCE: 19
aagcttcggc acgagcagac cagcatgggc atcaagatgg agacacattc tcaggtcttt   60
gtatacat                                                            68

<210> SEQ ID NO 20
<211> LENGTH: 22
<212> TYPE: DNA
<213> ORGANISM: Artificial Sequence
<220> FEATURE:
<223> OTHER INFORMATION: LC reverse primer 1
```

```
<400> SEQUENCE: 20
cattttgtct gactaggtgt cc                                          22

<210> SEQ ID NO 21
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 21

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser
            20                  25                  30

<210> SEQ ID NO 22
<211> LENGTH: 14
<212> TYPE: PRT
<213> ORGANISM: Artificial Sequence
<220> FEATURE:
<223> OTHER INFORMATION: The sequence is artificially synthesized

<400> SEQUENCE: 22

Trp Ile Val Gln Arg Pro Gly His Gly Leu Glu Trp Ile Gly
1               5                   10

<210> SEQ ID NO 23
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 23

Lys Ala Thr Phe Thr Ala Asp Thr Ser Ser Asn Thr Ala Ser Met Gln
1               5                   10                  15

Leu Ser Ser Leu Thr Ser Glu Asp Ser Ala Val Tyr Tyr Cys Ala Leu
            20                  25                  30

<210> SEQ ID NO 24
<211> LENGTH: 11
<212> TYPE: PRT
<213> ORGANISM: Artificial Sequence
<220> FEATURE:
<223> OTHER INFORMATION: The sequence is artificially synthesized

<400> SEQUENCE: 24

Trp Gly Gln Gly Thr Ser Val Thr Val Ser Ser
1               5                   10

<210> SEQ ID NO 25
<211> LENGTH: 30
<212> TYPE: PRT
<213> ORGANISM: Artificial Sequence
<220> FEATURE:
<223> OTHER INFORMATION: The sequence is artificially synthesized

<400> SEQUENCE: 25

Gln Val Gln Leu Gln Gln Ser Gly Ser Glu Leu Met Lys Pro Gly Ala
1               5                   10                  15

Ser Val Lys Val Ser Cys Lys Ala Ser Gly Tyr Thr Phe Thr
            20                  25                  30
```

<210> SEQ ID NO 26
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 26

Arg Ala Thr Phe Thr Ala Asp Thr Ser Thr Asp Thr Ala Ser Met Glu
1               5                   10                  15

Leu Ser Ser Leu Thr Ser Glu Asp Ser Ala Val Tyr Tyr Cys Ala Leu
            20                  25                  30

<210> SEQ ID NO 27
<211> LENGTH: 23
<212> TYPE: PRT
<213> ORGANISM: Artificial Sequence
<220> FEATURE:
<223> OTHER INFORMATION: The sequence is artificially synthesized

<400> SEQUENCE: 27

Asp Ile Val Met Thr Gln Ala Ala Pro Ser Val Ser Val Thr Pro Gly
1               5                   10                  15

Glu Ser Val Ser Ile Ser Cys
            20

<210> SEQ ID NO 28
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 28

Trp Phe Leu Gln Arg Pro Gly Gln Ser Pro Gln Leu Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: The sequence is artificially synthesized

<400> SEQUENCE: 29

Gly Val Pro Asp Arg Phe Ser Gly Ser Gly Ser Gly Thr Ala Phe Thr
1               5                   10                  15

Leu Lys Ile Arg Arg Val Glu Ala Glu Asp Val Gly Val Tyr Tyr Cys
            20                  25                  30

<210> SEQ ID NO 30
<211> LENGTH: 10
<212> TYPE: PRT
<213> ORGANISM: Artificial Sequence
<220> FEATURE:
<223> OTHER INFORMATION:
     The sequence is artificially synthesized

<400> SEQUENCE: 30

Phe Gly Ala Gly Thr Lys Leu Glu Leu Lys
1               5                   10

<210> SEQ ID NO 31
<211> LENGTH: 23
<212> TYPE: PRT

```
-continued

<213> ORGANISM: Artificial Sequence
<220> FEATURE:
<223> OTHER INFORMATION: The sequence is artificially synthesized

<400> SEQUENCE: 31

Asp Ile Val Met Thr Gln Ala Ala Pro Ser Leu Ser Val Thr Pro Gly
1               5                   10                  15

Glu Ser Val Ser Ile Ser Cys
            20

<210> SEQ ID NO 32
<211> LENGTH: 15
<212> TYPE: PRT
<213> ORGANISM: Artificial Sequence
<220> FEATURE:
<223> OTHER INFORMATION: The sequence is artificially synthesized

<400> SEQUENCE: 32

Trp Tyr Leu Gln Lys Pro Gly Gln Ser Pro Gln Leu Leu Ile Tyr
1               5                   10                  15
```